(12) United States Patent
Palese

(10) Patent No.: US 6,316,243 B1
(45) Date of Patent: Nov. 13, 2001

(54) GENETICALLY ENGINEERED ATTENUATED DOUBLE-STRANDED RNA VIRUSES

(76) Inventor: Peter Palese, 414 Highwood Ave., Leonia, NJ (US) 07605

( * ) Notice: Subject to any disclaimer, the term of this patent is extended or adjusted under 35 U.S.C. 154(b) by 0 days.

(21) Appl. No.: 08/470,106

(22) Filed: Jun. 6, 1995

Related U.S. Application Data

(60) Division of application No. 08/318,794, filed on Dec. 20, 1994, now Pat. No. 6,022,726, which is a continuation-in-part of application No. 07/868,596, filed on Apr. 14, 1992, now abandoned.

(30) Foreign Application Priority Data

Apr. 13, 1993 (WO) .................................. PCT/US93/03615

(51) Int. Cl.[7] .................................................. C12N 7/04
(52) U.S. Cl. .................. 435/236; 424/206.1; 424/215.1; 536/23.72
(58) Field of Search ................................. 435/236, 320.1; 424/206.1, 215.1; 536/23.72

(56) References Cited

U.S. PATENT DOCUMENTS

| | | |
|---|---|---|
| 3,992,522 | 11/1976 | Chanock et al. . |
| 4,053,583 | 10/1977 | Gits et al. . |
| 4,211,843 | 7/1980 | Debreuil et al. . |
| 4,215,051 | 7/1980 | Schroeder et al. . |
| 4,215,107 | 7/1980 | Buynak et al. . |
| 4,769,051 | 9/1988 | Paoletti et al. . |
| 4,859,587 | 8/1989 | Roizman . |
| 4,927,628 | * 5/1990 | Chanock et al. . |
| 5,006,335 | 4/1991 | Gluck et al. . |

FOREIGN PATENT DOCUMENTS

WO 89/06277   7/1989   (WO) .

OTHER PUBLICATIONS

Roizman et al., 1982, Dev. Biol. Standard 52: 287–304.
Meigner & Roizman, 1985, Antiviral Res., Suppl. 1: 259–265.
Meigner et al., 1987, Vaccines 87: 368–373.
Meigner et al., 1988, Virology 162: 251–254.
Meigner et al., J. Infectious Diseases 158: 602–614.
Luytjes et al., 1989, Cell 59: 1107–1113.
Enami et al., 1990, "Introduction of site–specific mutations into the genome of influenza virus", Proc. Natl. Acad. Sci. USA 87: 3802–3805.
Muster et al., 1991, Proc. Natl. Acad. Sci. USA 88: 5177–5181.
Enami & Palese, 1991, "High–efficiency formation of influenza virus transfectants", J. Virology 65(5): 2711–2713.
Racaniello, 1988, Adv. Virus Res. 34: 217–246.
Moss et al., 1989, J. Virology 63: 1884–1890.
Monica & Racaniello, 1989, J. Virology 63: 1377–1382.
Ren et al., 1991, J. Virology 65: 1377–1382.
Moss & Raceniello, 1991, EMBO J. 10: 1067–1074.
Cox et al., 1988, Virology 167(2): 554–567.
Li et al., 1992, J. Virology 66(1): 399–404.
Castrucci et al., 1992, J, Virology 66(8): 4647–4653.
Luo et al., 1992, "Mechanism of attenuation of a chimeric influenza A/B transfectant virus", J. Virology 66(8): 4679–4685.
Morimoto et al., 1989, Virology 173(2): 465–477.
Bassel–Duby et al., 1986, J. Virology 60(1): 64–67.
Nishikawa et al., 1988, J. Virology 62(11): 4022–4026.
Philpott et al., 1990, J. Virology 64(6): 2941–2947.
Lamb & Choppin, 1983, Ann. Rev. Biochem. 52: 467–506.
Kumar et al., 1990, Proc. Natl. Acad. Sci. USA 87: 1337–1341.
Bowie et al., 1990, Science 247: 1306–1310.
van der Werf et al., 1990, Vaccine 8: 269–277.
Els et al., 1985, Virology 142: 241–247.
Bos et al., 1986, Virology 154: 85–96.
Williams et al., 1989, J. Virology 63(1): 28–35.
Parvin et al., J. Virology 63(12): 5142–5152.
Lentz et al., 1987, Biochemistry 26: 5351–5358.
Burke et al., 1988, Nature 332: 81–82.
Racaniello et al., 1981, "Cloned poliovirus complementary DNA is infectious in mammalian cells", Science 214: 916–919.
Roner et al., 1990, "Reovirus RNA is infectious", Virology 179: 845–852.
Enami et al., 1991, "An influenza virus containing nine different RNA segments", Virology 185: 291–298.
Compans et al., 1970, "", in The Biology of Large RNA Viruses, Eds. Barry & Mahy, Academic Press, pp. 87–108.
Scholtissek et al., 1978, "A possible partial heterozygote of an influenza A virus", Virology 89: 506–516.
Smith & Hay, 1982, "Replication of the influenza virus genome", Virology 118: 96–108.
Enami et al., 1985, "Transcription and replication of eight RNA segments of influenza virus", Virology 142: 68–77.
Shapiro et al., 1987, "Influenza virus gene expression: Control mechanisms at early and late times of infection and nuclear–cytoplasmic transport of virus–specifc RNAs", J. Virology 61(3): 764–773.
Luo & Taylor, 1990, "Template switching by reverse transcriptase during DNA synthesis", J. Virology 64(9): 4321–4328.

(List continued on next page.)

*Primary Examiner*—Jeffrey Stucker

(57) ABSTRACT

The present invention relates to engineering attenuated viruses by altering a non-coding region or the coding sequence of a viral gene. Alterations of the non-coding regions which regulate transcription and/or replication are described. These alterations result in the down-regulation of the viral gene and an attenuation of the virus, either by the production of defective particles during replication, or by reducing the number of progeny virions produced during viral replication. Alterations of viral coding sequences are also described which result in a recombinant or chimeric attenuated virus.

6 Claims, 14 Drawing Sheets-

OTHER PUBLICATIONS

Figure 1:
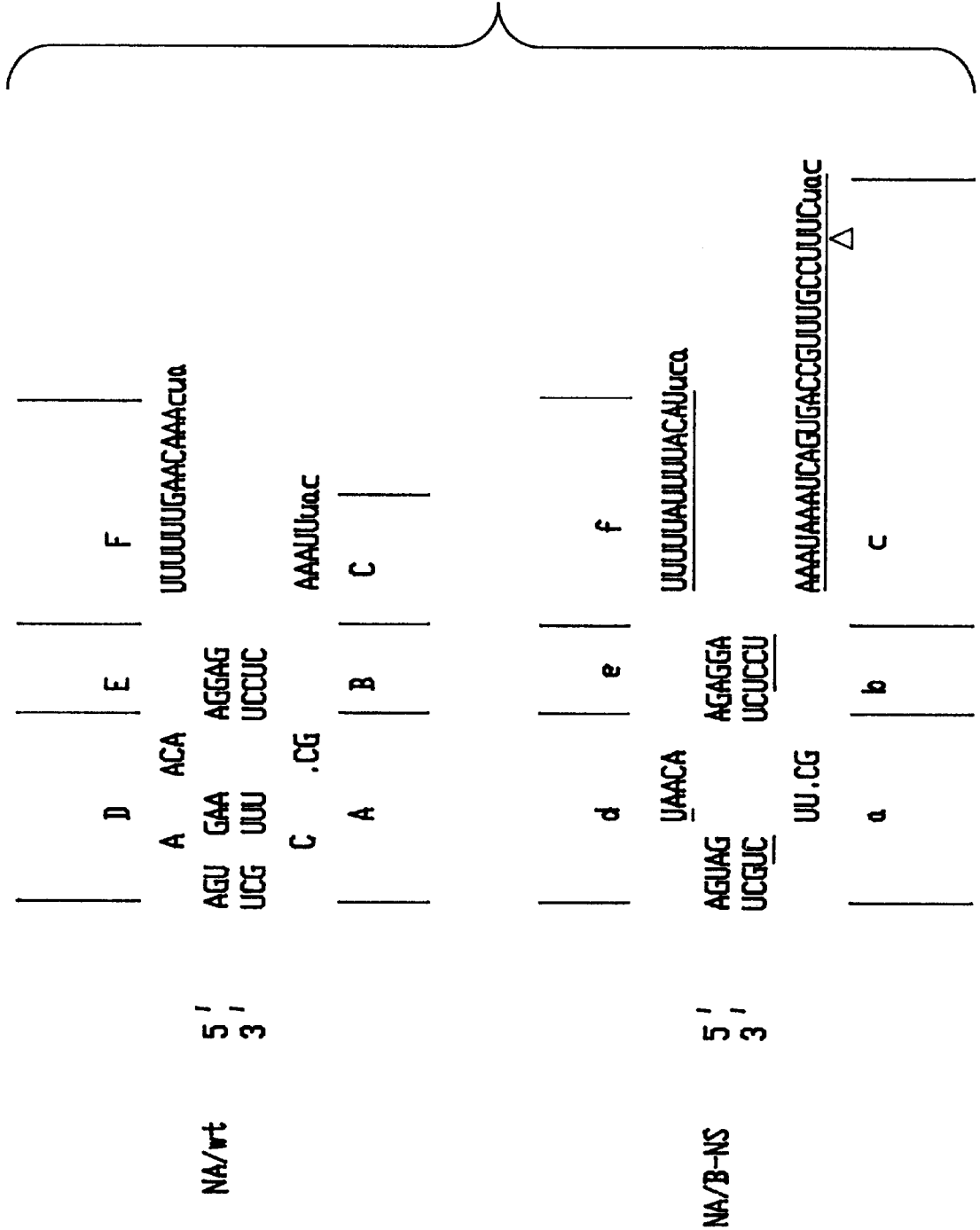

Luo et al., 1991, "The polyadenylation signal of influenza virus RNA involves a stretch of uridines followed by the RNA duplex of the panhandle structure", J. Virology 65: 2861–2867.

Laver & Valentine, 1969, "Morphology of the isolated hemagglutinin and neuraminidase subunits of influenza virus", Virology 38: 105–119.

Wrigley et al., 1973, "The size and shape of influenza virus neuraminidase", Virology 51: 525–529.

Palese et al., 1974, "Characterization of temperature sensitive influenza virus mutants defective in neuraminidase", Virology 61: 397–410.

Blok & Air, 1982, "Variation in the membrane–insertion and "stalk" sequences in eight subtypes of influenza type A virus neuraminidase", Biochemistry 21: 4001–4007.

Blok & Air, 1982, "Block deletions in the neuraminidase genes from some influenza A viruses of the N1 subtype", Virology 118: 229–234.

Hiti & Nayak, 1982, "Complete nucleotide sequence of the neuraminidase gene of human influenza virus A/WSN/33", J. Virology 41(2): 730–734.

Toyoda, et al., 1987, "Activation site of fusion glycoprotein between virulent and avirulent strains of Newcastle disease virus." Virology 158(1): 242–247.

Colman, 1989, "Neuraminidase: Enzyme and antigen", in The Influenza Viruses, Ed. Krug, Plenum Press, pp. 175–218.

Lamb et al. Fields et al ed*Fields Virology*, 3rd ed. 1996, vol. 1 p. 1355 "Orthomyxoviridae : The Viruses and their replication".*

Nibert et al. Fields et al.ed.*Fields Virology*, 3rd ed. 1996, vol. 2. p 1559 "Reoviruses and Their Replication".*

* cited by examiner

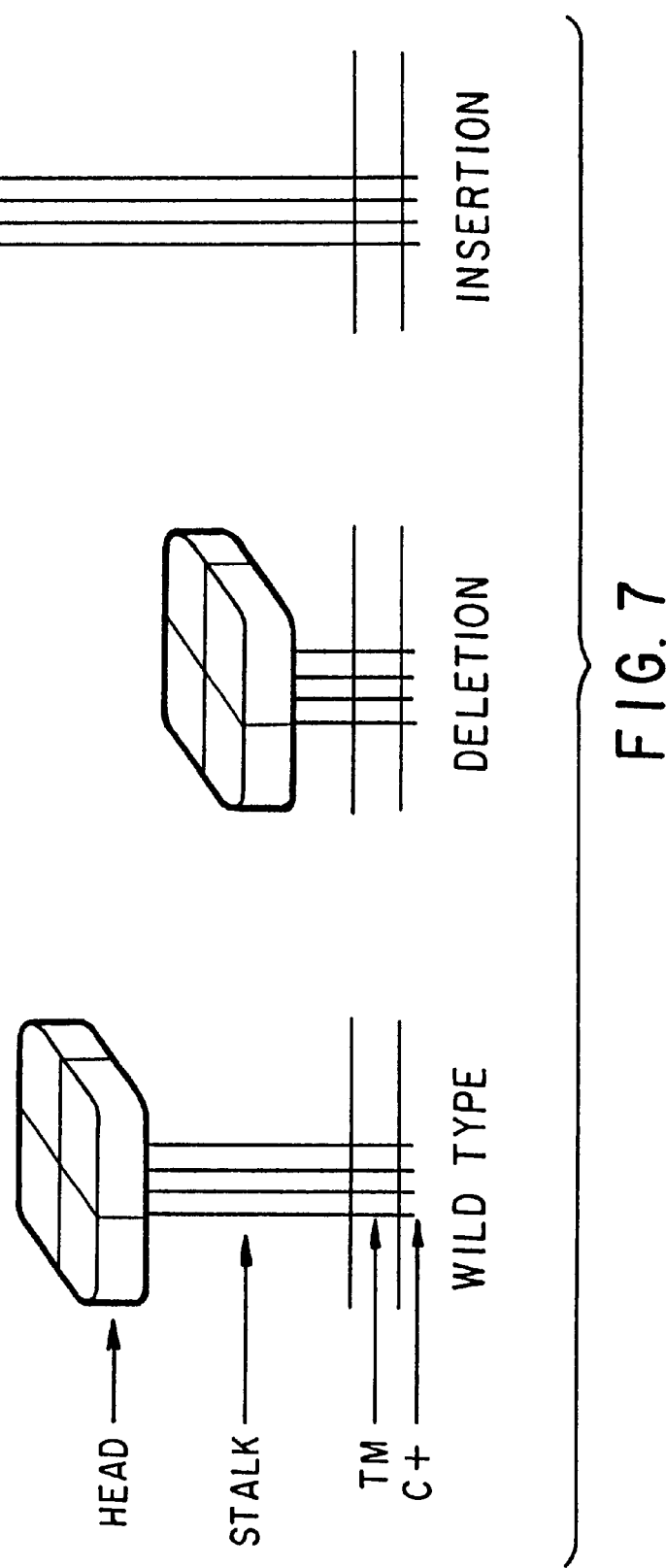

SEQUENCE LISTING (1) GENERAL INFORMATION:

(iii) NUMBER OF SEQUENCES: 36

(2) INFORMATION FOR SEQ ID NO: 1:

(i) SEQUENCE CHARACTERISTICS:
      (A) LENGTH: 12 amino acids
      (B) TYPE: amino acid
      (D) TOPOLOGY: unknown (ii) MOLECULE TYPE: peptide (xi) SEQUENCE DESCRIPTION: SEQ ID NO: 1:

Asn Glu Asp Ser Tyr Val Pro Ser Ala Glu Gln Ile
1            5                10

(2) INFORMATION FOR SEQ ID NO: 2:

(i) SEQUENCE CHARACTERISTICS:

(A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 2:

GGGAACAATT AGGTCAGAAG T                                              21

(2) INFORMATION FOR SEQ ID NO: 3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 3:

GTGGCAATAA CTAATCGGTC A                                              21

(2) INFORMATION FOR SEQ ID NO: 4:

(i) SEQUENCE CHARACTERISTICS:
        (A) LENGTH: 10 amino acids
        (B) TYPE: amino acid
        (D) TOPOLOGY: unknown (ii) MOLECULE TYPE: peptide (xi) SEQUENCE DESCRIPTION: SEQ ID NO: 4:

Pro Ala Ser Thr Thr Asn Lys Asp Lys Leu
1               5                   10

(2) INFORMATION FOR SEQ ID NO: 5:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

CCTGGGTGTC CTTC                                                      14

(2) INFORMATION FOR SEQ ID NO: 6:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 6:

CCCCACTGCA GATG                                                      14

(2) INFORMATION FOR SEQ ID NO: 7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:

CAAGGCAGCA CCGGCAACTC GAGTCTTTGT CCCATC                                      36

(2) INFORMATION FOR SEQ ID NO: 8:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 8:

CACGGATGGG ACAAAGACTC GAGTTGCCGG TGCTGC                                      36

(2) INFORMATION FOR SEQ ID NO: 9:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 9:

GCGCGCTCGA GAGGCTGCCT TGG                                                    23

(2) INFORMATION FOR SEQ ID NO: 10:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 10:

GTAAAACGAC GGCCAGT                                                           17

(2) INFORMATION FOR SEQ ID NO: 11:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 11:

GCGCGCTCGA GTTGCCGGTA GTATGGTTTT G                                           31

(2) INFORMATION FOR SEQ ID NO: 12:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 12:

GCGCGCCACG GCAAAGAGAT GAATTGTTGC ATATTCC                37

(2) INFORMATION FOR SEQ ID NO: 13:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 13:

GCGCGCTCGA GTTGCCGGTT CCGGTTTGAA T                       31

(2) INFORMATION FOR SEQ ID NO: 14:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 14:

GCGCGCCACG GATGGGCGAA AGAGATGATT GGCCGGTTAA TATC          44

(2) INFORMATION FOR SEQ ID NO: 15:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 15:

CTTGGATGGG ACAAAGACTC GAGTTGCCGG TGCTGC                   36

(2) INFORMATION FOR SEQ ID NO: 16:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 16:

GCGCGCCGTG GGACCGGAAA TC                                  22

(2) INFORMATION FOR SEQ ID NO: 17:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 17:

AGCCCACCCA CGG                                            13

(2) INFORMATION FOR SEQ ID NO: 18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 18:

```
GTCAATCTGT ATGGTAGTCG G                                              21
```

(2) INFORMATION FOR SEQ ID NO: 19:

(i) SEQUENCE CHARACTERISTICS:
        (A) LENGTH: 54 base pairs
        (B) TYPE: nucleic acid
        (C) STRANDEDNESS: single
        (D) TOPOLOGY: unknown (ii) MOLECULE TYPE: RNA (xi) SEQUENCE DESCRIPTION: SEQ ID NO: 19:

```
UUACAAACAA GUUUUUGAG GAACAAAGAU GAUCGUUUGC GUCCUCAAAC UUAC           54
```

(2) INFORMATION FOR SEQ ID NO: 20:

(i) SEQUENCE CHARACTERISTICS:
        (A) LENGTH: 53 base pairs
        (B) TYPE: nucleic acid
        (C) STRANDEDNESS: single
        (D) TOPOLOGY: unknown (ii) MOLECULE TYPE: RNA (xi) SEQUENCE DESCRIPTION: SEQ ID NO: 20:

```
AGUAGAAACA AGGAGUUUUU UGAACAAACU ACAUUUAAAC UCCUGCUUUC GCU           53
```

(2) INFORMATION FOR SEQ ID NO: 21:

(i) SEQUENCE CHARACTERISTICS:
        (A) LENGTH: 78 base pairs
        (B) TYPE: nucleic acid
        (C) STRANDEDNESS: single
        (D) TOPOLOGY: unknown (ii) MOLECULE TYPE: RNA (xi) SEQUENCE DESCRIPTION: SEQ ID NO: 21:

```
AGUAGUAACA AGAGGAUUUU UAUUUUACAU UCACAUCUUU CCGUUUGCCA GUGACUAAAU    60
AAAUCCUCUG CUUCUGCU                                                  78
```

(2) INFORMATION FOR SEQ ID NO: 22:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO: 22:

```
Cys Asp Ser Leu Leu Pro Ala Arg Ser Trp Ser Tyr Ile
1               5                   10
```

(2) INFORMATION FOR SEQ ID NO: 23:

(i) SEQUENCE CHARACTERISTICS:
    (A) LENGTH: 17 amino acids
    (B) TYPE: amino acid
    (D) TOPOLOGY: unknown (ii) MOLECULE TYPE: peptide (xi) SEQUENCE DESCRIPTION: SEQ ID NO: 23:

```
Cys Asn Glu Asp Ser Tyr Val Pro Ser Ala Glu Gln Ile Trp Ser Tyr
1               5                   10                  15

Ile
```

(2) INFORMATION FOR SEQ ID NO: 24:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO: 24:

```
Trp Leu Thr Lys Lys Gly Asp Ser Tyr Pro Lys Leu Thr
1               5                   10
```

(2) INFORMATION FOR SEQ ID NO: 25:

(i) SEQUENCE CHARACTERISTICS:
        (A) LENGTH: 23 amino acids
        (B) TYPE: amino acid
        (D) TOPOLOGY: unknown (ii) MOLECULE TYPE: peptide (xi) SEQUENCE DESCRIPTION: SEQ ID NO: 25:

```
Trp Leu Thr Lys Lys Gly Pro Ala Ser Thr Thr Asn Lys Asp Lys Leu
1               5                   10                  15

Asp Ser Tyr Pro Lys Leu Thr
                20
```

(2) INFORMATION FOR SEQ ID NO: 26:

(i) SEQUENCE CHARACTERISTICS:
        (A) LENGTH: 45 amino acids
        (B) TYPE: amino acid
        (D) TOPOLOGY: unknown (ii) MOLECULE TYPE: peptide (xi) SEQUENCE DESCRIPTION: SEQ ID NO: 26:

```
His Ser Ile Gln Thr Gly Asn Gln Asn His Thr Gly Ile Cys Asn Gln
1               5                   10                  15

Gly Ser Ile Thr Tyr Lys Val Val Ala Gly Gln Asp Ser Thr Ser Val
                20                  25                  30

Ile Leu Thr Gly Asn Ser Ser Leu Cys Pro Ile Arg Gly
                35                  40                  45
```

(2) INFORMATION FOR SEQ ID NO: 27:

(i) SEQUENCE CHARACTERISTICS:
        (A) LENGTH: 29 amino acids
        (B) TYPE: amino acid
        (D) TOPOLOGY: unknown (ii) MOLECULE TYPE: peptide (xi) SEQUENCE DESCRIPTION: SEQ ID NO: 27:

```
His Ser Ile Gln Thr Gly Asn Gln Asn His Thr Gly Ile Cys Asn Gln
 1               5                  10                  15

Gly Ser Thr Gly Asn Ser Ser Leu Cys Pro Ile Arg Gly
                20                  25
```

(2) INFORMATION FOR SEQ ID NO: 28:

(i) SEQUENCE CHARACTERISTICS:
        (A) LENGTH: 17 amino acids
        (B) TYPE: amino acid
        (D) TOPOLOGY: unknown (ii) MOLECULE TYPE: peptide (xi) SEQUENCE DESCRIPTION: SEQ ID NO: 28:

```
His Ser Ile Gln Thr Gly Asn Gln Asn His Thr Gly Ile Cys Asn Arg
 1               5                  10                  15

Gly
```

(2) INFORMATION FOR SEQ ID NO: 29:

(i) SEQUENCE CHARACTERISTICS:
        (A) LENGTH: 27 amino acids
        (B) TYPE: amino acid
        (D) TOPOLOGY: unknown (ii) MOLECULE TYPE: peptide (xi) SEQUENCE DESCRIPTION: SEQ ID NO: 29:

```
His Ser Ile Gln Thr Gly Asn Gln Asn His Thr Gly Ile Cys Asn Gln
 1               5                  10                  15

Gly Ser Leu Ser Ser Leu Cys Pro Ile Arg Gly
                20                  25
```

(2) INFORMATION FOR SEQ ID NO: 30:

(i) SEQUENCE CHARACTERISTICS:
        (A) LENGTH: 22 amino acids
        (B) TYPE: amino acid
        (D) TOPOLOGY: unknown (ii) MOLECULE TYPE: peptide (xi) SEQUENCE DESCRIPTION: SEQ ID NO: 30:

```
His Ser Ile Gln Thr Gly Asn Gln Asn His Thr Gly Ile Cys Asn Asn
 1               5                  10                  15

Ser Ser Leu Cys Arg Gly
                20
```

(2) INFORMATION FOR SEQ ID NO: 31:

(i) SEQUENCE CHARACTERISTICS:
        (A) LENGTH: 22 amino acids
        (B) TYPE: amino acid
        (D) TOPOLOGY: unknown (ii) MOLECULE TYPE: peptide (xi) SEQUENCE DESCRIPTION: SEQ ID NO: 31:

```
His Ser Ile Gln Thr Gly Asn Gln Asn His Thr Thr Gly Asn Ser Ser
 1               5                  10                  15

Leu Cys Pro Ile Arg Gly
                20
```

(2) INFORMATION FOR SEQ ID NO: 32:

(i) SEQUENCE CHARACTERISTICS:
        (A) LENGTH: 17 amino acids
        (B) TYPE: amino acid
        (D) TOPOLOGY: unknown (ii) MOLECULE TYPE: peptide (xi) SEQUENCE DESCRIPTION: SEQ ID NO: 32:

His Ser Ile Gln Thr Gly Thr Gly Asn Ser Ser Leu Cys Pro Ile Arg
1               5                   10                  15
Gly (2) INFORMATION FOR SEQ ID NO: 33:

(i) SEQUENCE CHARACTERISTICS:
        (A) LENGTH: 19 amino acids
        (B) TYPE: amino acid
        (D) TOPOLOGY: unknown (ii) MOLECULE TYPE: peptide (xi) SEQUENCE DESCRIPTION: SEQ ID NO: 33:

Cys Asn Gln Gly Ser Thr Gly Asn Ser Ser Leu Cys Pro Ile Gln Gly
1               5                   10                  15
Ser Ile Thr (2) INFORMATION FOR SEQ ID NO: 34:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (xi) SEQUENCE DESCRIPTION: SEQ ID NO: 34:

Cys Asn Gln Gly Ser Thr Gly Asn Ser Ser Leu Cys Pro Ile Gln Gly
1               5                   10                  15
Ser Thr Gly Asn Ser Ser Leu Cys Pro Ile Gln Gly Ser Ile Thr
                20                  25                  30

(2) INFORMATION FOR SEQ ID NO: 35:

(i) SEQUENCE CHARACTERISTICS:
        (A) LENGTH: 43 amino acids
        (B) TYPE: amino acid
        (D) TOPOLOGY: unknown (ii) MOLECULE TYPE: peptide (xi) SEQUENCE DESCRIPTION: SEQ ID NO: 35:

Gln Thr Gly Asn Gln Asn His Thr Gly Ile Cys Asn Gln Gly Ser Ile
1               5                   10                  15
Thr Tyr Lys Val Val Ala Gly Gln Asp Ser Thr Ser Val Ile Leu Thr
                20                  25                  30
Gly Asn Ser Ser Leu Cys Pro Ile Arg Gly Thr
                35                  40

(2) INFORMATION FOR SEQ ID NO: 36:

(i) SEQUENCE CHARACTERISTICS:
        (A) LENGTH: 44 amino acids
        (B) TYPE: amino acid
        (D) TOPOLOGY: unknown -continued

```
    (ii) MOLECULE TYPE: peptide (xi) SEQUENCE DESCRIPTION: SEQ ID NO: 36:

His Ser Ile Gln Thr Gly Asn Gly Asn His Thr Gly Ile Cys Asn Gln
1               5                   10                  15

Gly Ser Ile Thr Val Lys Trp Ala Gly Gln Asp Ser Thr Ser Val Ile
            20                  25                  30

Leu Thr Gly Gln Ser Ser Leu Ser Pro Ile Arg Gly
            35                  40
```

GENETICALLY ENGINEERED ATTENUATED DOUBLE-STRANDED RNA VIRUSES

This is a division of application Ser. No. 08/318,794 filed Dec. 20, 1994, now U.S. Pat. No. 6,022,726, which is a continuation-in-part of application Ser. No. 07/868,596, filed Apr. 14, 1992 now abandoned.

This is a Continuation-In-Part of Ser. No. 07/868,596 filed Apr. 14, 1992, which is incorporated by reference herein in its entirety.

The work reflected in this application was supported, in part, by a grant from the National Institutes of Health, and the Government may have certain rights in the invention.

1. INTRODUCTION

The present invention relates to engineering attenuated viruses by altering a non-coding region or the coding sequence of a viral gene. Alterations of the non-coding regions which regulate transcription and/or replication are described. These alterations result in the down-regulation of the viral gene and an attenuation of the virus, either by the production of defective particles during replication, or by reducing the number of progeny virions produced during viral replication. Alterations of viral coding sequences are also described which result in a recombinant or chimeric attenuated virus.

2. BACKGROUND OF THE INVENTION

Inactivated virus vaccines are prepared by "killing" the viral pathogen, e.g., by heat or formalin treatment, so that it is not capable of replication. Inactivated vaccines have limited utility because they do not provide long lasting immunity and, therefore, afford limited protection. An alternative approach for producing virus vaccines involves the use of attenuated live virus vaccines. Attenuated viruses are capable of replication but are not pathogenic, and, therefore, provide for longer lasting immunity and afford greater protection. However, the conventional methods for producing attenuated viruses involve the chance isolation of host range mutants, many of which are temperature sensitive; e.g., the virus is passaged through unnatural hosts, and progeny viruses which are immunogenic, yet not pathogenic, are selected.

Recombinant DNA technology and genetic engineering techniques, in theory, would afford a superior approach to producing an attenuated virus since specific mutations could be deliberately engineered into the viral genome. However, the genetic alterations required for attenuation of viruses are not known or predictable. In general, the attempts to use recombinant DNA technology to engineer viral vaccines have mostly been directed to the production of subunit vaccines which contain only the protein subunits of the pathogen involved in the immune response, expressed in recombinant viral vectors such as vaccinia virus or baculovirus. More recently, recombinant DNA techniques have been utilized in an attempt to produce herpes virus deletion mutants or polioviruses which mimic attenuated viruses found in nature or known host range mutants. Until very recently, the negative strand RNA viruses were not amenable to site-specific manipulation at all, and thus could not be genetically engineered.

3. SUMMARY OF THE INVENTION

The present invention relates to the production of attenuated viruses using recombinant DNA techniques. At least two approaches for engineering attenuated viruses are described. One approach involves engineering alterations of a non-coding region of the virus that regulates transcription and/or replication of a viral gene so that at least one of the viral genes is down regulated. This approach may be applied to a number of different viruses and is advantageously used to engineer segmented viruses where down regulation of the synthesis of one viral segment results in the generation of defective particles during each round of viral replication so that the progeny viruses demonstrate attenuated characteristics. In non-segmented viruses, the down regulation of a viral gene can result in a decrease in the number of infectious virions produced during replication, so that the virus demonstrates attenuated characteristics.

A second approach involves engineering alterations of a viral coding region so that the viral protein expressed is altered by the insertion, deletion or substitution of an amino acid residue or an epitope and an attenuated chimeric virus is produced.

The attenuated viruses of the invention may advantageously be used safely in live virus vaccine formulation. As used herein, the term "attenuated" virus refers to a virus which is infectious but not pathogenic; or an infectious virus which may or may not be pathogenic, but which either produces defective particles during each round of replication or produces fewer progeny virions than does the corresponding wild type virus during replication. Pathogenic viruses which are engineered to produce defective particles or a reduced number of progeny virions are "attenuated" in that even though the virus is capable of causing disease, the titers of virus obtained in a vaccinated individual will provide only subclinical levels of infection.

4. DESCRIPTION OF THE FIGURES

FIG. 1. The noncoding sequences of the NA segments of influenza A/WSN/33 virus and of the NA/B-NS transfectant virus. The 5'- and 3'-terminal sequences are drawn in a panhandle structure, which consists of two base-paired stems and one mismatched internal-loop in the middle. The noncoding nucleotides of the chimeric NA gene of the NA/B-NS virus are derived from the NS gene of influenza B/Lee virus. The large letters indicate nucleotides in the 5' and 3' terminal regions (containing 13 and 12 nucleotides, respectively) which are different for the two NA genes. The panhandle structure of the wild type virus NA gene is divided into regions A/D, B/E, and C/F, and that of the attenuated gene into a/d, b/e, and c/f. Regions B/E and b/e contain the second stem regions of the NA and the NA/B-NS genes, respectively. The open triangle marks the altered Kozak sequence in the NA gene of the NA/B-NS virus.

Figure 2A:
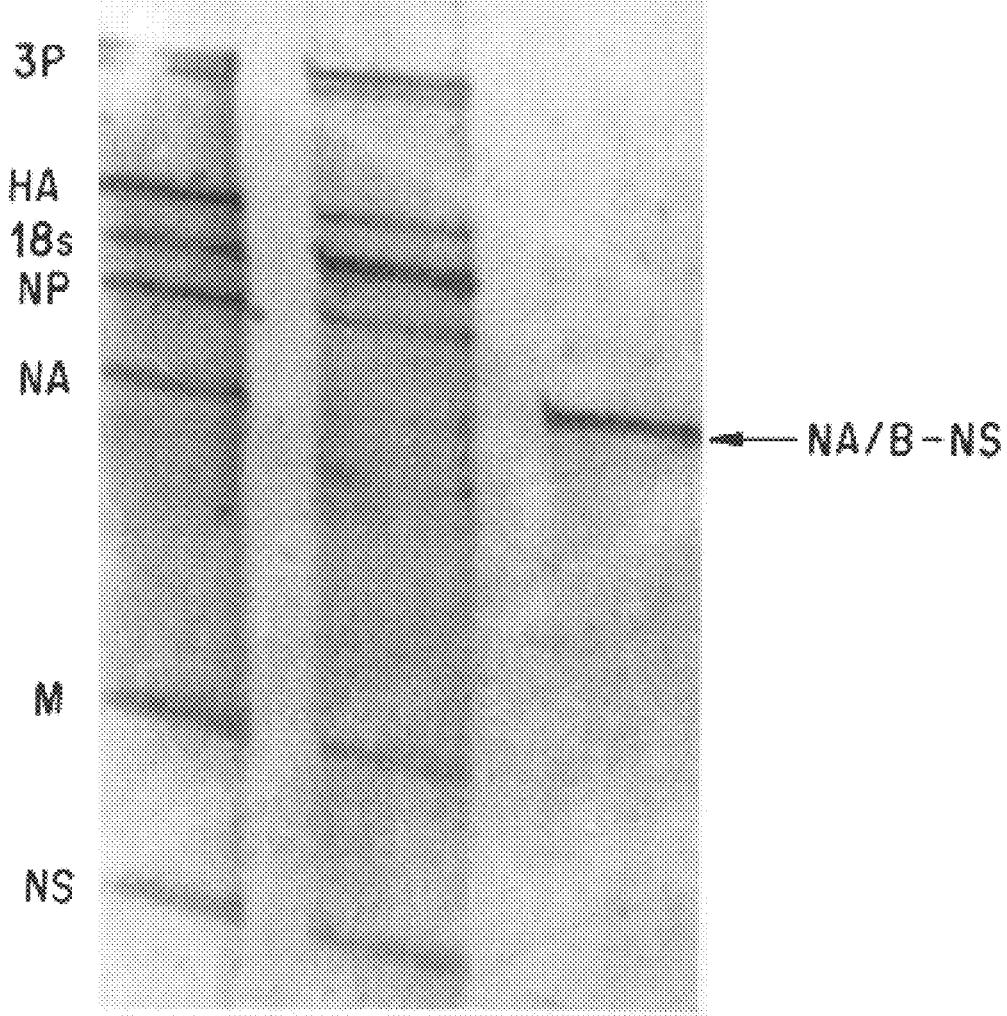
Figure 2B:
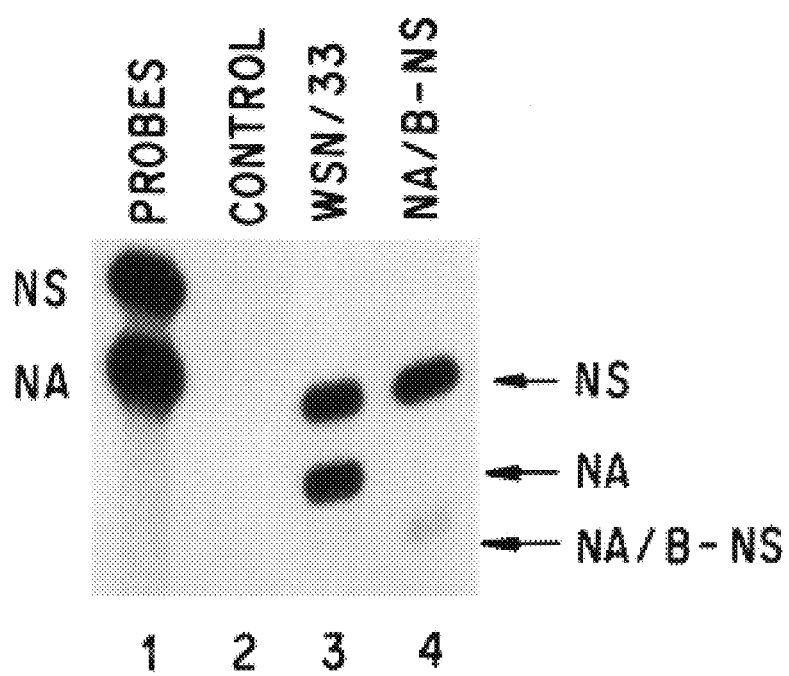
Figure 2C:
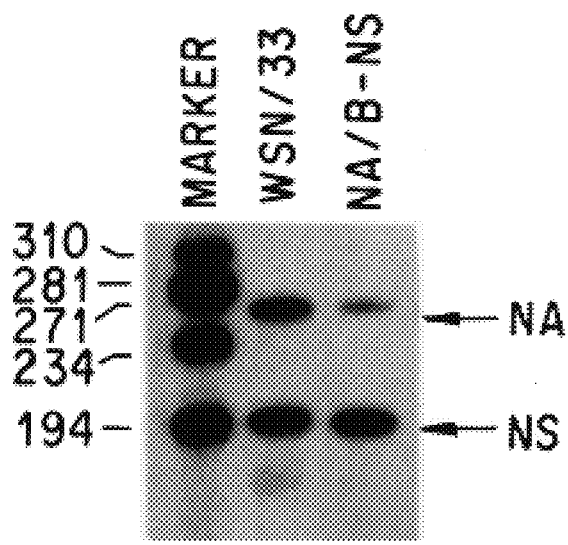

FIGS. 2A–2C. Characterization of the RNA of the NA/B-NS virus. FIG. 2A. RNA electrophoresis. The RNAs extracted from purified viruses were analyzed on a 3% polyacrylamide gel containing 7.7 M urea and visualized by silver staining. Lane 1, RNA of influenza A WSN/33 virus; lane 2, RNA of NA/B-NS transfectant virus; lane 3, RNA obtained by run-off transcription from plasmid Pt-NA/B-NS which produces the chimeric NA RNA. FIG. 2B. Analysis of NA RNA in virions by ribonuclease protection assay (RPA). 50 ng of RNA extracted from purified virus was used in the hybridization reaction with positive sense NS and NA specific riboprobes as described in Materials and Methods. The protected probes were electrophoresed on a 6% acrylamide gel containing 7 M urea. Lane 1: riboprobes without RNase A/T$_1$ digestion; lane 2: riboprobes following RNase A/T$_1$ digestion; lane 3: riboprobes protected by the RNA of influenza A/WSN/33 virus; and lane 4: riboprobes protected by the RNA of NA/B-NS transfectant virus. FIG. 2C. Quantitation of NA-specific RNA in virus by primer extension. The vRNA extracted from either WSN/33 virus (lane 2) or NA/B-NS transfectant virus (lane 3) was reverse transcribed by Rnase H minus reverse transcriptase using NS and NA segment specific primers as described in Materials and Methods. The products for the NS RNAs are 195 nt long and those for the NA RNAs approximately 260 nt long. The products were analyzed on a 6% polyacrylamide gel containing 7M urea. Size markers are shown on the left.

Figure 3A:
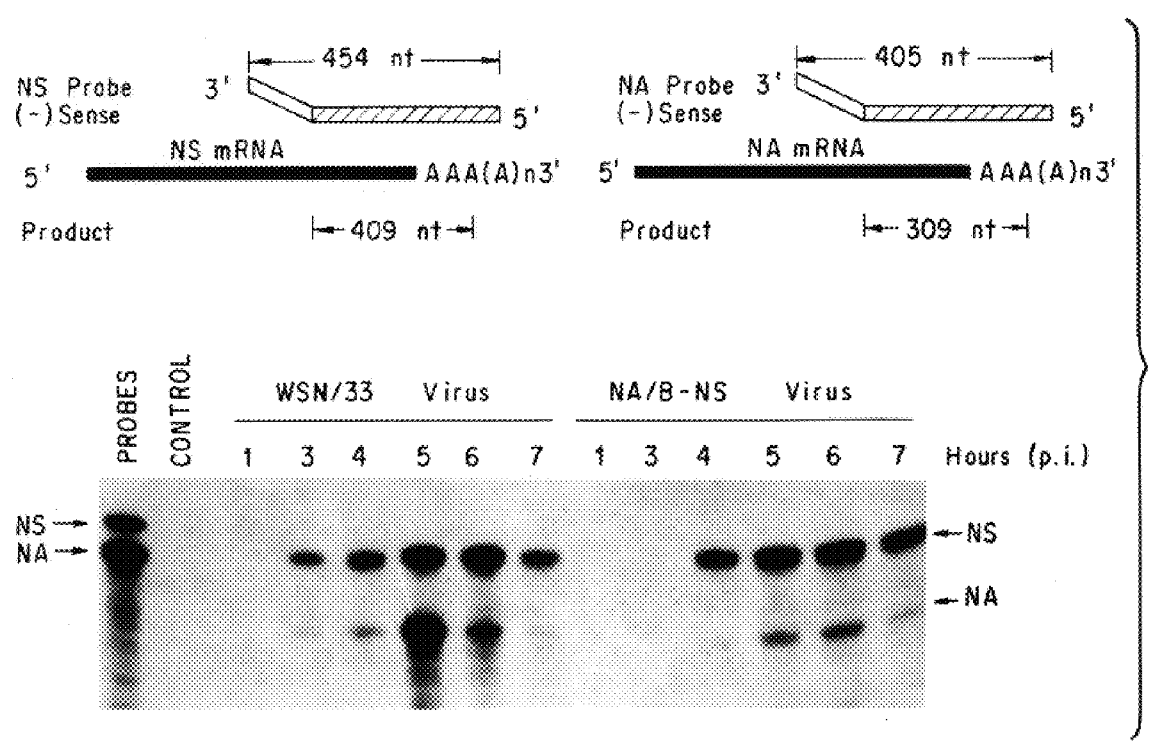
Figure 3B:
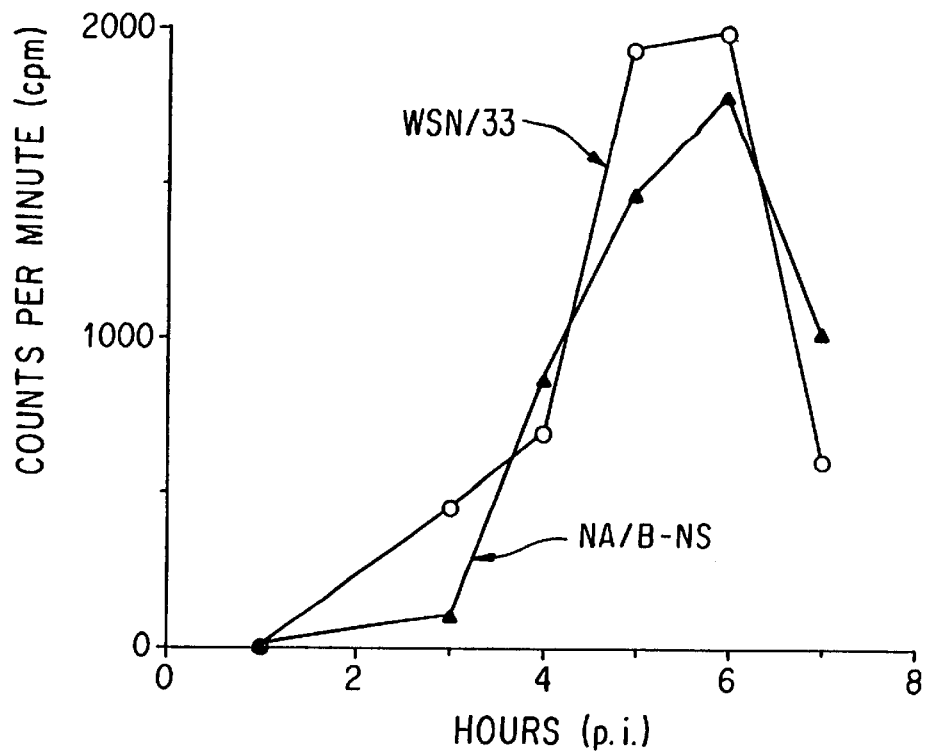
Figure 3C:
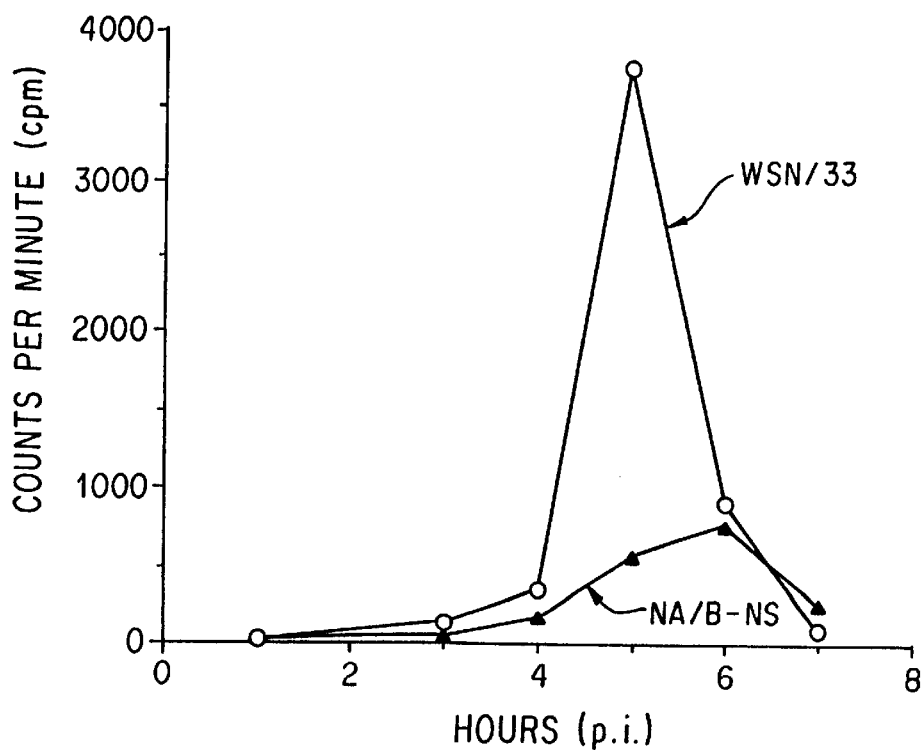

FIGS. 3A–3C. Time course of mRNA synthesis in MDBK cells. FIG. 3A. Quantitation of NA- and NS-specific mRNAs at different times p.i. by ribonuclease protection assay (RPA). The diagram on the top schematically illustrates the procedure. Both NS and NA probes are minus sense, and contain sequences corresponding to the 3'-terminal side of the cRNA, flanked by vector sequences at the 3'-terminus as indicated by the open rectangles. The sizes of the probes are shown on the top, and the sizes of the resulting products are indicated at the bottom of the diagram. The time points (hrs) are indicated on the top. The positions of probes and products on the gel are indicated by arrows at the left and right, respectively. FIG. 3B. Time course of NS-specific MRNA synthesis. The amount of the NS MRNA was measured by direct counting the radioactivity (counts per minute) in the corresponding band excised from the gel shown in FIG. 3A. FIG. 3C. Comparison of NA-specific MRNA synthesis of transfectant virus and A/WSN/33 virus in infected cells. The amount of mRNA for each time point was determined as described in FIG. 3B.

Figure 4:
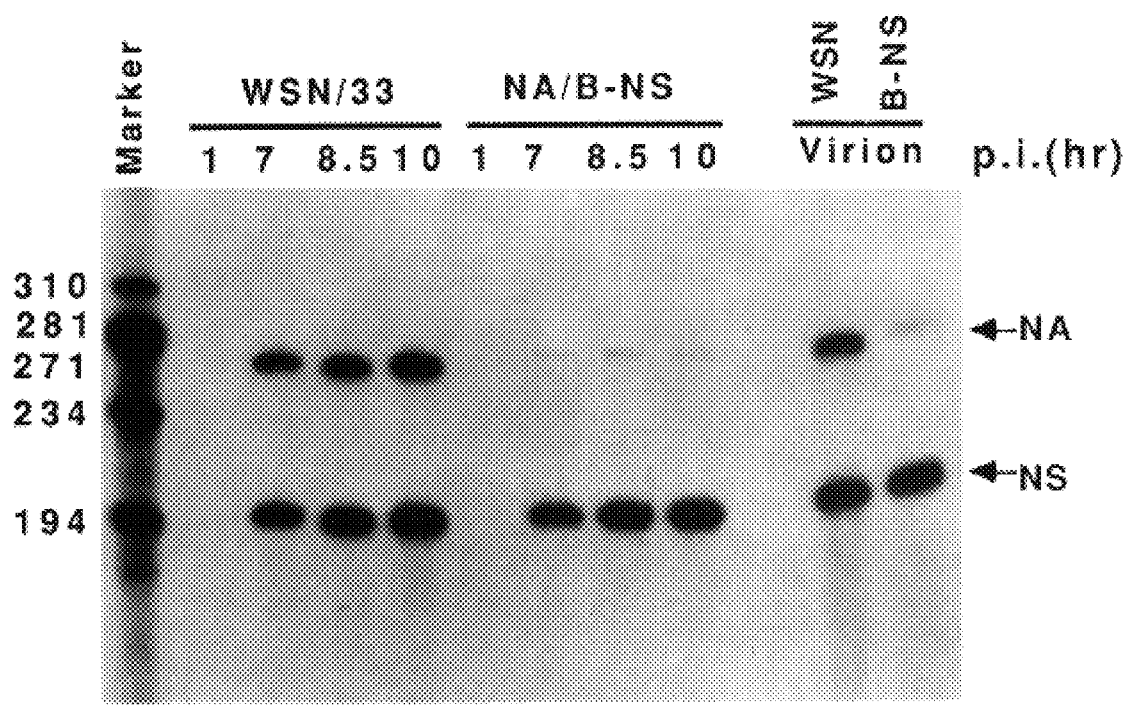

FIG. 4. Analysis of NA-specific vRNA synthesis in infected cells by primer extension. RNA isolated from infected cells was reverse transcribed using reverse transcriptase and NA and NS vRNA-specific primers, as described in Materials and Methods. vRNAs extracted from purified virus were used as control (right). The resulting products were displayed on a 6% acrylamide denaturing gel. The reverse transcripts of the NS RNAs are 195 nt long and those of the NA-specific segments are approximately 260 nt long, as indicated by arrows at the right. The numbers on the top indicate the times (hrs) postinfection. Virion represents the RNA obtained from purified virus.

Figure 5A:
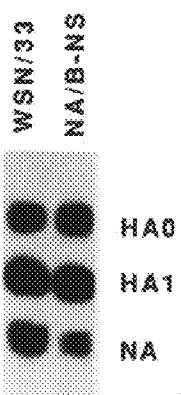
Figure 5B:
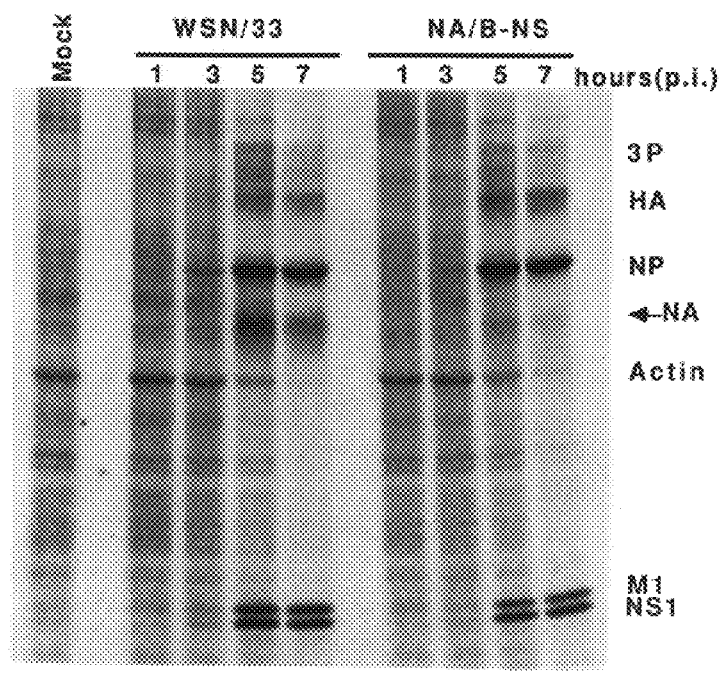

FIGS. 5A–5B. Analysis of NA protein in virion and in infected cells. FIG. 5A. Western analysis of NA protein in virion. As described in Materials and Methods, a monoclonal antibody directed against carbohydrate was used to quantitate the glycoprotein in the viruses. The proteins are indicated by HA0 (uncleaved HA), HA1 (subunit 1 of HA) AND NA at the right. FIG. 5B. Viral proteins synthesized in infected cells. At different times postinfection (hrs p.i.), the viral proteins were labelled with $^{35}$S[cysteine] for 30 minutes, and analyzed on a 10% Laemmli gel. The different proteins are marked at the right. The position of the NA protein is indicated by an arrow. The amount of NA protein was determined by counting the gel a radioanalytic AMBIS imaging system using NP and M1 proteins as controls.

FIG. 6. Vector for construction of chimeric HA molecules. FIG. 6A. Chimeric HA/ME1 malaria construct. FIG. 6B. H1 Chimeric HA/polio H2.

FIG. 7. Schematic Structure of Neuraminidase (NA). Tetrameric NA inserted in viral membrane is depicted. Ct, cytoplasmic tail; TM, transmembrane domain; Stalk, stalk region; Head, the globular domain most distal to the viral membrane.

Figure 8:
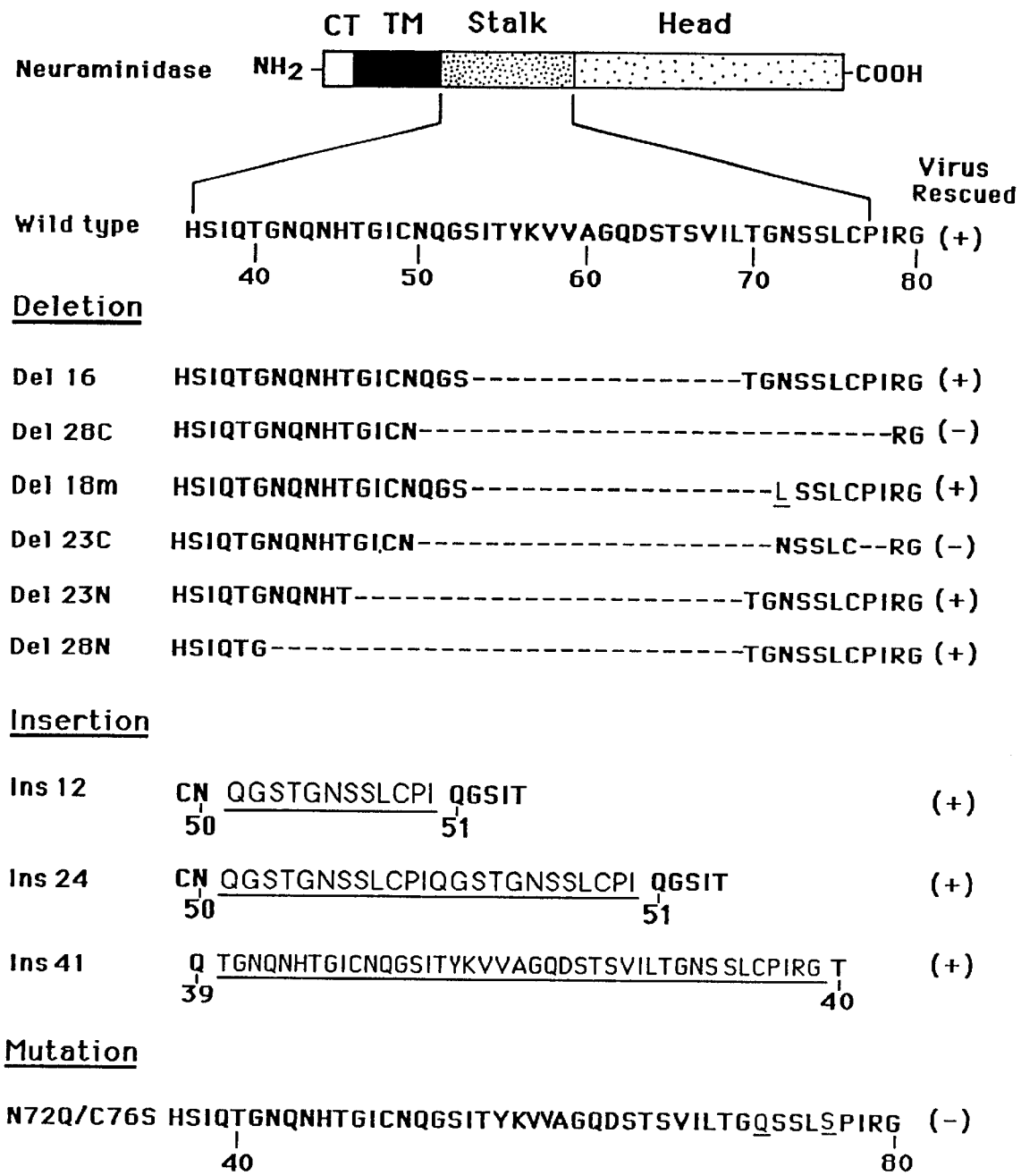

FIG. 8. Diagram of neuraminidase mutants. The four domains of the neuraminidase molecule are indicated: CT, cytoplasmic tail; TM, transmembrane domain; Stalk, stalk region and Head, the globular domain most distal to the viral membrane. The numbering system of the amino acids is according to Hiti and Nayak, 1982, J. Virol. 41:730–734. Deletions are as indicated, and insertions and mutations in the stalk region are underlined. The diagram is not drawn to scale. (+) indicates that infectious virus was recused following transfection of the mutant RNA.

Figure 9:
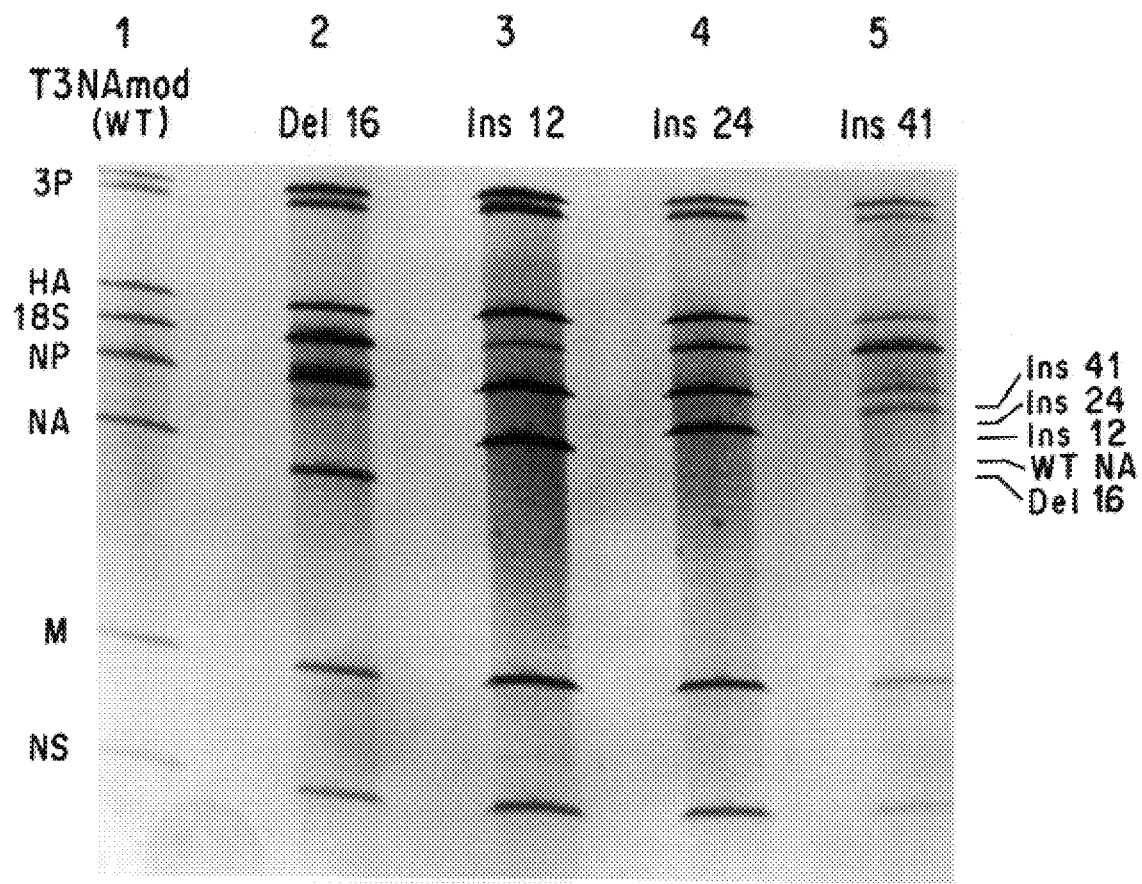

FIG. 9. Gel analysis of vRNAs extracted from purified viruses. Viruses and vRNAs were prepared as described in Section 9.1. 200 ng virion RNA was analyzed on a 2.8% polyacrylamide gel containing 7.7 M urea. The RNA segments were visualized by silver staining as described previously (Enami et al., 1990, Proc. Natl. Acad. Sci. USA 87:3802–3805). Each RNA segment is indicated at the left. Lane 1, wild type transfected virus. Lane 2, Del 16 mutant virus. Lane 3, Ins 12 mutant virus. Lane 4, Ins 24 mutant virus. Lane 5, Ins 41 mutant virus. Arrows indicate the position of the NA genes in each of the RNA preparations.

Figure 10:
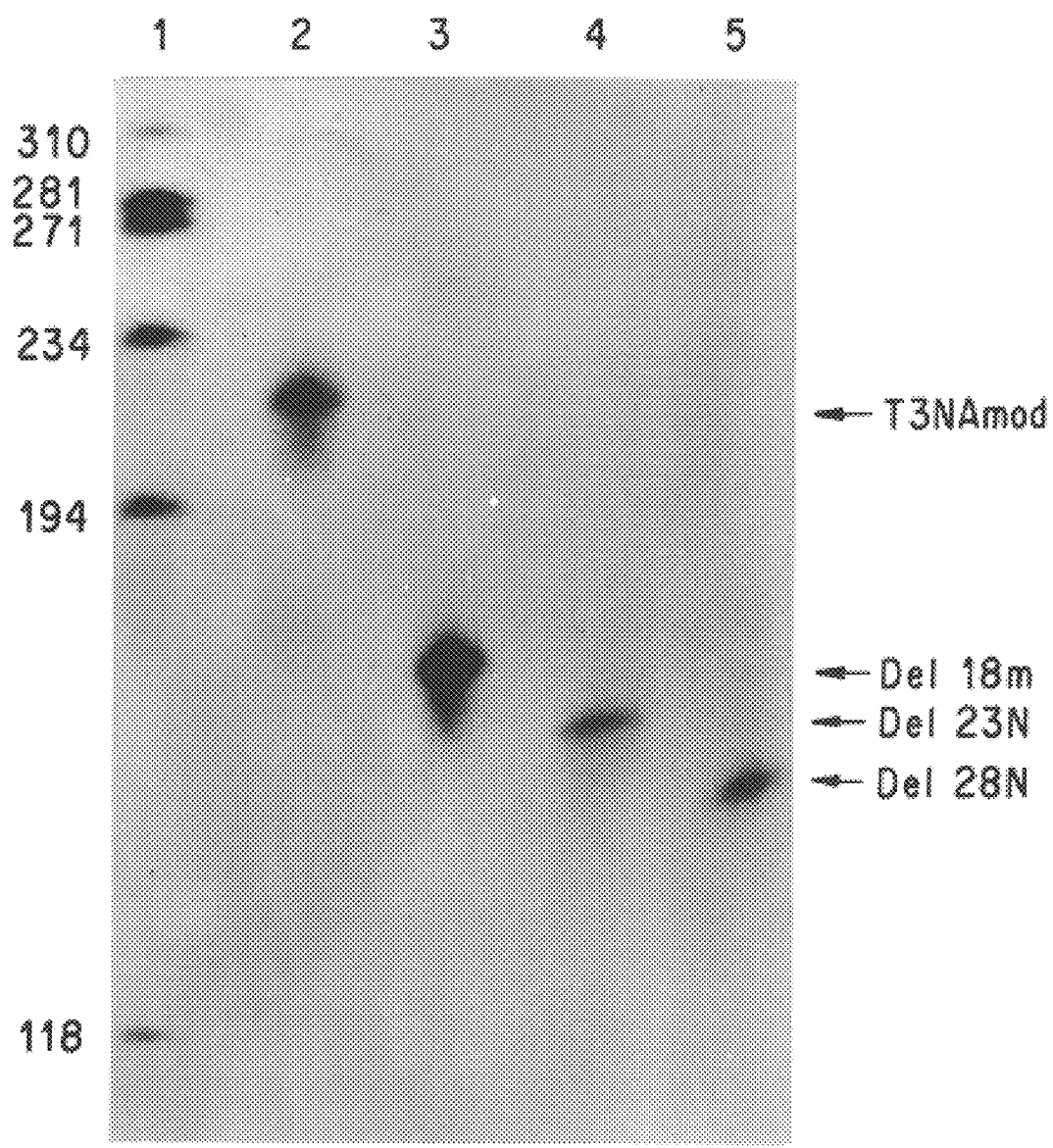

FIG. 10. Analysis of vRNA by reverse transcription and PCR. RNA extracted from purified virus was reverse transcribed and the NA gene-specific transcripts were then amplified by PCR as described in Section 9.1. The PCR products labelled with gamma [$^{32}$P] ATP were analyzed on a 6% polyacrylamide gel containing 7 M urea (Luo et al., 1991, J. Virol. 65:2861–2867). The expected products for wild type NA, Del 18m, Del 23N and Del 28N mutant NAs were 214, 160, 145 and 130 nucleotides long, respectively. PhiX174 RF DNA/Hae III fragments (BRL, Bethesda, MD) were labelled with gamma $^{32}$[P] ATP and were used as size markers. The sizes of the DNA fragments are indicated at the left. Lane 1, size marker. Lane 2, product of wild type NA (T3NAmod). Lane 3, product of Del 18m mutant NA. Lane 4, product of Del 23N mutant NA. Lane 5, product of Del 28N mutant NA. Arrows indicated the position of the PCR products.

Figure 11A:
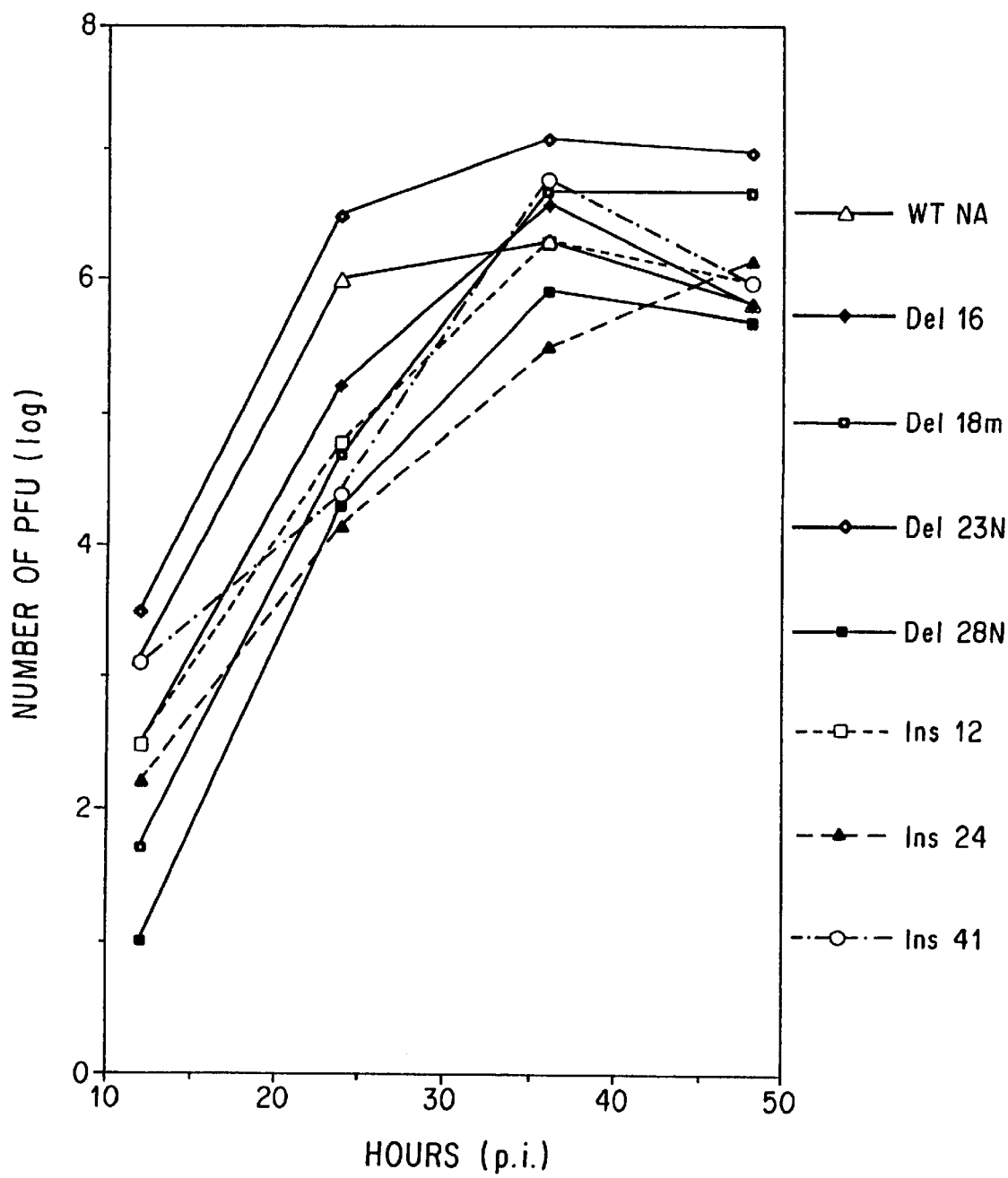
Figure 11B:
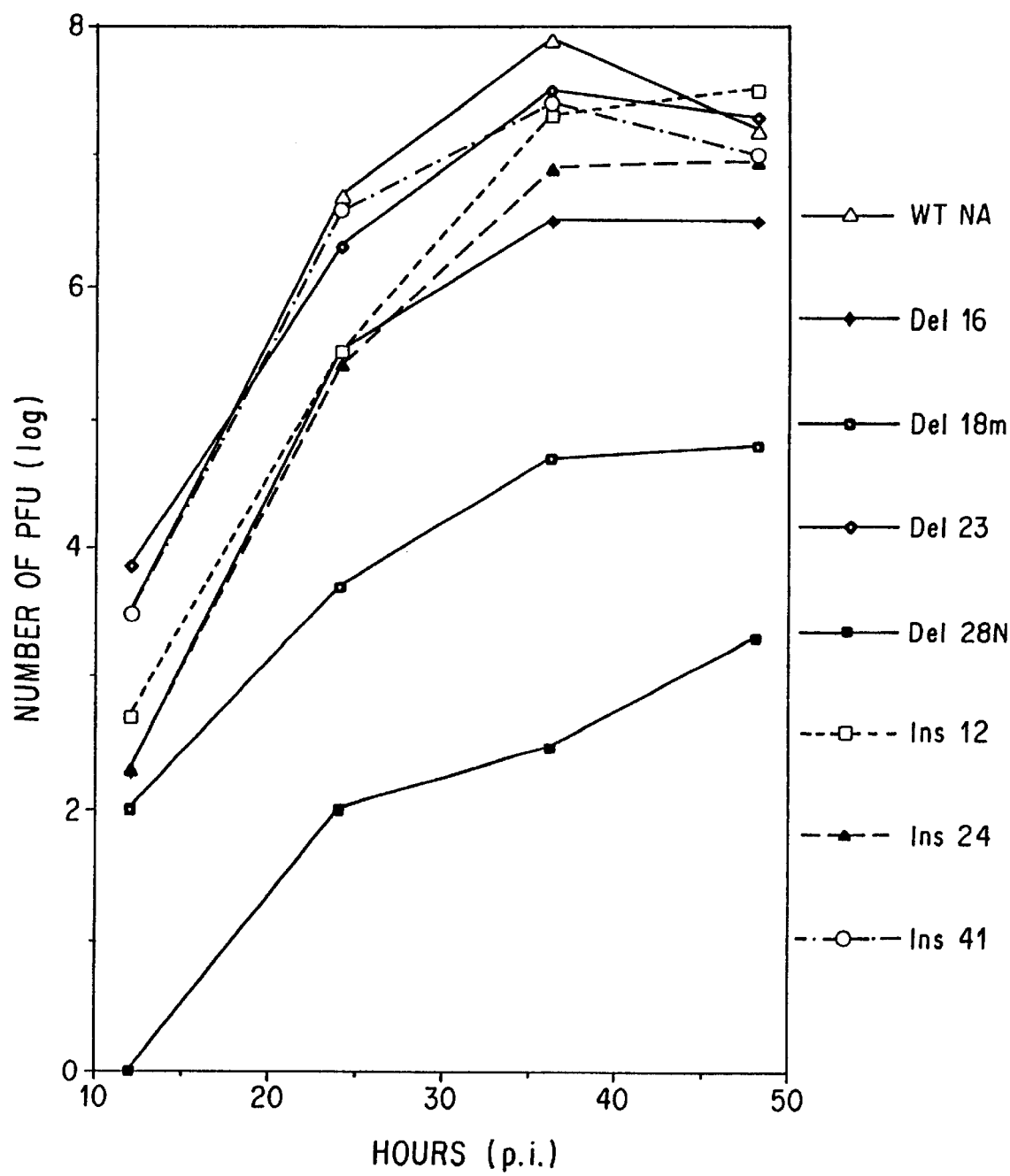

FIGS. 11A–11B. Growth curves of transfectant viruses in MDBK (FIG. 11A.) and MDCK. (FIG. 11B.) cells. Cells were infected with wild type or mutant viruses at the m.o.i. of 0.001 and virus titers of supernatant collected at the indicated times were determined as described in Section 9.1.

5. DETAILED DESCRIPTION OF THE INVENTION

The present invention relates to genetically engineered attenuated viruses, and methods for their production. Recombinant DNA techniques can be utilized to engineer site specific mutations into one or more noncoding regions of the viral genome which result in the down-regulation of one or more viral genes. Alternatively, recombinant DNA techniques can be used to engineer a mutation, including but not limited to an insertion, deletion, or substitution of an amino acid residue(s) or an epitope(s) into a coding region of the viral genome so that altered or chimeric viral proteins are expressed by the engineered virus. The invention is based, in part, on the discovery that the down regulation of a viral gene in segmented viruses results in the production of defective particles at each round of replication, so that the virus demonstrates attenuated characteristics. In non-segmented viruses, the down-regulation of a viral gene may result in the production of fewer progeny virions than would be generated by the corresponding wild type virus. The alterations of the viral proteins described also result in attenuation for reasons which are less well understood.

Many methods may be used to introduce the live attenuated virus formulations to a human or animal subject to induce an immune response; these include, but are not limited to, oral, intradermal, intramuscular, intraperitoneal, intravenous, subcutaneous and intranasal routes. It is preferable to introduce the chimeric virus vaccine via its natural route of infection.

Any virus may be engineered in accordance with the invention to produce an attenuated strain suitable for use as a safe live-virus vaccine, including but not limited to viruses belonging to the families set forth in Table I below.

TABLE I

FAMILIES OF HUMAN AND ANIMAL VIRUSES

| VIRUS CHARACTERISTICS | VIRUS FAMILY |
|---|---|
| dsDNA | |
| Enveloped | Poxviridae |
| | Irididoviridae |
| | Herpesviridae |
| Nonenveloped | Adenoviridae |
| | Papovaviridae |
| | Hepadnaviridae |
| ssDNA | |
| Nonenveloped | Parvoviridae |
| dsRNA | |
| Nonenveloped | Reoviridae |
| | Birnaviridae |
| sRNA | |
| Enveloped | |
| Positive-Sense Genome | |
| No DNA Step in Replication | Togaviridae |
| | Flaviviridae |
| | Coronaviridae |
| | Hepatitis C Virus |
| DNA Step in Replication | Retroviridae |
| Negative-Sense Genome | |
| Non-Segmented Genome | Paramyxoviridae |
| | Rhabdoviridae |
| | Filoviridae |
| Segmented Genome | Orthoinyxoviridae |
| | Bunyaviridae |
| | Arenaviridae |
| Nonenveloped | Picornaviridae |
| | Calciviridae |

Abbreviations used: ds = double stranded; ss = single stranded; enveloped = possessing an outer lipid bilayer derived from the host cell membrane; positive-sense genome = for RNA viruses, genomes that are composed of nucleotide sequences that are directly translated on ribosomes, = for DNA viruses, genomes that are composed of nucleotide sequences that are the same as the mRNA; negative-sense genome = genomes that are composed of nucleotide sequences complementary to the positive-sense strand.

DNA viruses (e.g., vaccinia, adenoviruses, baculovirus) and positive strand RNA viruses (e.g., poliovirus) may be readily engineered using recombinant DNA techniques which are well known in the art (e.g., see U.S. Pat. No. 4,769,330 to Paoletti; U.S. Pat. No. 4,215,051 to Smith; Racaniello et al., 1981, Science 214: 916–919). Until recently, however, negative strand RNA viruses (e.g., influenza) were not amenable to site specific genetic manipulation because the viral RNAs are not infectious. However, a recently developed technique, called "reverse genetics," allows the engineering and production of recombinant negative strand RNA viruses.

The reverse genetics technique involves the preparation of synthetic recombinant viral RNAs that contain the non-coding regions of the negative strand virus which are essential for the recognition of viral RNA by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. A more efficient transfection is achieved if the viral polymerase proteins are present during in vitro transcription of the synthetic RNAS. The synthetic recombinant RNPs can be rescued into infectious virus particles. The foregoing techniques are described in U.S. Pat. No. 5,166,057 and in Enami & Palese, 1991, J. Virol. 65: 2711–2713, each of which is incorporated by reference herein in its entirety), and influenza A viruses containing insertions, deletions and mutations with the stalk portion of the NA gene, one of which changes acts as a host range mutant. Using the reverse genetics technique, the following recombinant negative-strand viruses were engineered: an influenza virus containing nine different RNA segments; a chimeric influenza A virus (NA/B-NS) in which the noncoding region of the NA gene was replaced by that belonging to an influenza B virus NS gene; an influenza A virus with chimeric hemagglutinins containing epitopes from different influenza subtypes (Enami et al., 1991, Virology 185: 291–298; Muster et al., 1991, Proc. Natl. Acad. Sci. USA 88: 5711–5781; copending application Ser. No. 07/841,310 filed Feb. 3, 1992; and Li et al., 1992, J. Virol. 66: 399–404; each of which is incorporated by reference herein in its entirety); and influenza A viruses containing insertions, deletions, and mutations within the stalk portion of the NA gene, one of which acts as a host range mutant. The invention is discussed in more detail in the subsections below and the examples infra. For clarity, the details of the invention are described using influenza. However, the principles may be analogously applied to construct other attenuated viruses.

5.1. DOWN-REGULATION OF VIRAL GENES

In accordance with the invention, a non-coding regulatory region of a virus can be altered to down-regulate any viral gene, e.g. reduce transcription of its mRNA and/or reduce replication of vRNA (viral RNA), so that an attenuated virus is produced.

This approach, while applicable to any virus, is particularly attractive for engineering viruses with segmented genomes; i.e., viruses in which the genome is divided into segments that are packaged into virions. For example, the segmented genome of influenza A virus (an orthomyxovirus) consists of eight molecules of linear negative-sense ssRNAs which encode ten polypeptides, including: the RNA-directed RNA polymerase proteins (PB2, PB1 and PA) and nucleoprotein (NP) which form the nucleocapsid; two surface glycoproteins which project from the envelope: hemagglutinin (HA) and neuraminidase (NA); and nonstructural proteins (NS1 and NS2) whose function is unknown. The termini of each segment contain the non-coding regions essential for recognition by viral polymerase and for packaging signals necessary to generate a mature virion. The sequence of the termini is highly conserved among all eight segments. As another example, the segmented genome of reoviruses consists of 10 to 12 segments of linear dsRNA which encode 6 to 10 major structural polypeptides, a transcriptase and other enzymes.

Alterations of non-coding regulatory regions of segmented viruses which result in down-regulation of replication of a viral gene segment, and/or down-regulation of transcription of a viral gene will result in the production of defective particles in each round of replication; i.e. particles which package less than the full complement of viral segments required for a fully infectious, pathogenic virus. Therefore, the altered virus will demonstrate attenuated characteristics in that the virus will shed more defective particles than wild type particles in each round of replication. However, since the amount of protein synthesized in each round is similar for both wild type virus and the defective particles, such attenuated viruses are capable of inducing a good immune response.

The foregoing approach is equally applicable to non-segmented viruses, where the down regulation of transcription of a viral gene will reduce the production of its mRNA and the encoded gene product. Where the viral gene encodes a structural protein, e.g., a capsid, matrix, surface or envelope protein, the number of particles produced during replication will be reduced so that the altered virus demonstrates attenuated characteristics; e.g., a titer which results in subclinical levels of infection. For example, a decrease in viral capsid expression will reduce the number of nucleocapsids packaged during replication, whereas a decrease in expression of the envelope protein may reduce the number and/or infectivity of progeny virions. Alternatively, a decrease in expression of the viral enzymes required for replication, e.g., the polymerase, replicase, helicase, and the like, should decrease the number of progeny genomes generated during replication. Since the number of infectious particles produced during replication are reduced, the altered viruses demonstrate attenuated characteristics. However, the number of antigenic virus particles produced will be sufficient to induce a vigorous immune response.

Any alteration of the regulatory non-coding regions which decrease their efficiency or strength may be engineered in accordance in the invention. For example, the strength of viral promoters can be reduced by alterations in the stem structure. In the experiments detailed herein, specific nucleotide changes in the second stem structure of the promoter (B/E in FIG. 1) at the termini of the vRNAs which make up the panhandle structure of segmented negative-strand strand RNA viruses, such as influenza, were found to be responsible for the down-regulation of the synthesis of one vRNA segment. In particular, the UCCU/AGGA nucleotides of the chimeric influenza mutant NA/DeF/AbC (Section 7.2.1, Table III) are the critical base pairs involved. (The comparable base pairs in the wild type are CUC/GAG).

This base pair combination was introduced into the non-coding regulatory regions for other viral genes. Results indicate that the chimeric viruses so produced are also attenuated. Apparently, changes in this second stem structure lead to a reduction in vRNA synthesis of the viral segment, which is accompanied by a reduction in the number of infectious particles containing a full complement of all eight RNA segments. It should also be noted that the reversion rate of the changed stem structure is extremely low, since reversion would require the simultaneous change of two nucleotides.

While the engineered reduction in vRNA or mRNA produces attenuation, this is not accompanied by a significant reduction in the viral protein specified by the gene. In fact, it may be desirable to engineer strong translation signals into the viral gene so that the gene transcripts which are present at low concentrations are efficiently translated into viral proteins required to provide some degree of replication.

The experiments described in the examples detailed infra were designed to understand the molecular mechanism underlying the changed growth characteristics of the chimeric NA/B-NS virus, as well as other engineered viruses described herein (e.g., RAM 3, HA/malaria ME 1, and HA/poliovirus 1) with the aim of developing a prototype for live virus vaccines. The NA/B-NS is a transfectant influenza A virus containing a chimeric NA gene in which the non-coding sequences are identical to those in the NS gene of influenza B/Lee virus described in copending application Ser. No. 07/841,310, filed Feb. 3, 1992 now abandoned, by Palese et al.; and in Muster et al., 1991, Proc. Natl. Acad. Sci. USA 88: 5177–5181 each of which is incorporated by reference herein in its entirety). This virus has many unique growth characteristics in tissue culture and it is highly attenuated in mice.

Several lines of evidence obtained from the experiments described herein indicate that the cis elements derived from the influenza B/Lee virus gene are responsible for the dramatic effects on transcription and replication of the chimeric NA gene of the NA/B-NS transfectant virus. It was found that the NA gene had a six-fold lower representation in the purified viral preparation than did the remaining seven RNAs (see Sections 6.2.2 and 6.2.4, infra). This strikingly lower representation of one RNA is compatible with the finding that the NA/B-NS transfectant virus has an approximately 5- to 10-fold lower infectious particle to physical particle ratio than wild type virus (see Section 6.2.1, infra). It is assumed that an infectious virus would require the presence of a full complement of all eight influenza virus RNA segments. Many of the NA/B-NS progeny virus, however, lack an NA gene, so that more defective particles are formed than is the case in a wild type virus infection. It is not clear whether this 5- to 10-fold reduction in titer is only the reflection of the lower representation of the NA gene or whether other factors also play a role. For example, some viruses may contain defective interfering RNAs which would lower the infectivity titer of the preparation.

The mRNA synthesis of the NA is also considerably reduced in transfectant virus-infected cells (see Section 6.2.4, infra). Surprisingly, this does not lead to a commensurate reduction in protein synthesis. Both virus-infected cells and purified virus show only a two-fold lower level of NA protein relative to that of wild type-infected cells or of purified wild type virus itself (see Section 6.2.3, infra). This higher than expected level of NA protein in the transfectant virus may be the result of a good Kozak sequence present in the chimeric NA gene. The chimeric NA gene has an A in the −3 position instead of the U found in the wild type NA RNA (see open triangle in FIG. 1). The data also indicate that the two-fold reduction in NA activity does not significantly influence the pathogenicity of the virus, since other transfectant viruses were constructed (e.g., NAM 3 shown below) in which the expression of the NA gene is down regulated by a factor of 10 without affecting virus growth in tissue culture (see Section 7.2.2 and Table IV, infra):

```
     AG.A      A            UUUGAACAAACAUU
   AGU     AAC.. AGGAGUUU
   UCG     UUG   UCCUCAAA
     ...U      CG           CUUAC
```

It should be noted that in the transfectant virus, expression of the other seven genes is not altered. Specifically, the NA/B-NS virus produces the same level of HA protein as found in wild type virus and comparable amounts of HA are packaged into the envelope of the virus. It appears that the attenuation characteristic is best explained by the lower synthesis of NA-specific vRNA and by the resulting lower representation of particles containing a full complement of the eight RNA segments.

How influenza A virus packages its eight RNA genome segments remains an interesting question. In the past, two different mechanisms were proposed for the packaging of influenza virus RNAs: one suggests that the eight RNAs are selectively packaged and the other that viral RNAs are packaged randomly (Compans et al., 1970, In The Biology Of Large RNA Viruses, Barry & Mahy, Eds., pp. 87–108, Academic Press, New York; Lamb & Choppin, 1983, Ann. Rev. Biochem. 467–506; Smith & Hay, 1982, Virology 118: 96–108). Evidence is now accumulating to support the random packaging mechanism. The random packaging theory originated from the fact that influenza viruses have a low ratio of infectious particles to physical particles. If one assumes that an average of 11 RNAs are packaged per virion, the expected ratio is compatible with that found in vivo (Enami et al., 1991, Virology 185: 291–298). This model was also supported by the finding of a reassortant virus which contained two copies of the same segment derived from two different viruses (Scholtissek, 1978, Virology 89: 506–516), and further support for this theory came from a more recent report which described an influenza A virus which required nine RNAs in order to be infectious (Enami et al., 1991, Virology 185: 291–298). The data described in the examples, infra, concerning the characterization of the NA/B-NS transfectant virus also seem to favor the random packaging mechanism rather than the selective one. The lower level of chimeric NA RNA found in virions is consistent with the reduction of its synthesis in infected cells. In a selective packaging model, it would be expected that approximately equimolar amounts of chimeric NA RNA would be packaged into virus particles.

In summary, the experiments described infra, indicate that influenza viruses for which the synthesis of a vRNA segment is down-regulated produce defective particles during replication. Since the proteins of this virus are unaltered as compared to wild type virus, attenuation must be the result of inefficient cis-acting signals. This principal of attenuation may be applied analogously to other viruses with segmented genomes. For example, the introduction of modifications into the noncoding sequences of rotavirus genes or of genes of other segmented dsRNA viruses (Roner et al., 1990, Virology 179: 845–852) should also allow the pathogenicity of these viruses to be altered.

5.2. ALTERATION OF VIRAL PROTEINS

An alternative way to engineer attenuated viruses involves the introduction of an alteration, including but not limited to an insertion, deletion or substitution of one or more amino acid residues and/or epitopes into one or more of the viral proteins. This may be readily accomplished by engineering the appropriate alteration into the corresponding viral gene sequence. Any change that alters the activity of the viral protein so that viral replication is modified or reduced may be accomplished in accordance with the invention.

For example, alterations that interfere with but do not completely abolish viral attachment to host cell receptors and ensuing infection can be engineered into viral surface antigens or viral proteases involved in processing to produce an attenuated strain. According to this embodiment, viral surface antigens can be modified to contain insertions, substitution or deletions of one or more amino acids or epitopes that interfere with or reduce the binding affinity of the viral antigen for the host cell receptors. This approach offers an added advantage in that a chimeric virus which expresses a foreign epitope may be produced which also demonstrates attenuated characteristics. Such viruses are ideal candidates for use as live recombinant vaccines. For example, heterologous gene sequences that can be engineered into the chimeric viruses of the invention include, but are not limited to, epitopes of human immunodeficiency virus (HIV) such as gp120; hepatitis B virus surface antigen (HBsAg); the glycoproteins of herpes virus (e.g., gD, gE); VP1 of poliovirus; and antigenic determinants of nonviral pathogens such as bacteria and parasites to name but a few.

In this regard, influenza is an ideal system in which to engineer foreign epitopes, because the ability to select from thousands of influenza virus variants for constructing chimeric viruses obviates the problem of host resistance or immune tolerance encountered when using other virus vectors such as vaccinia. In addition, since influenza stimulates a vigorous secretory and cytotoxic T cell response, the presentation of foreign epitopes in the influenza background may also provide for the secretory immunity and cell-mediated immunity. By way of example, the insertion, deletion or substitution of amino acid residues in the HA protein of influenza can be engineered to produce an attenuated strain. In this regard, alterations to the B region or E region of HA may be utilized. In accordance with this approach, the malarial epitope (ME 1) of *Plasmodium yoelii* (NEDSYVPSAEQI) (SEQ ID NO: 1) was introduced into the antigenic site E of the hemagglutinin of influenza. The resulting chimeric virus has a 500- to 1,000-fold lower $LD_{50}$ (lethal dose 50) than that of wild type virus when assayed in mice. In another embodiment, the major antigenic determinant of poliovirus type 1, i.e., the BC loop of the VP1 of poliovirus type 1 (PASTTNKDKL) (SEQ ID NO: 4) was engineered into the B region of the influenza HA protein. This chimeric virus is also attenuated (e.g., see Section 8, infra).

In another embodiment, alterations of viral proteases required for processing viral proteins can be engineered to produce attenuation. Alterations which affect enzyme activity and render the enzyme less efficient in processing, should affect viral infectivity, packaging, and/or release to produce an attenuated virus. For example, alterations to the NA protein of influenza can be engineered to reduce NA enzyme activity and decrease the number and/or infectivity of progeny virus released during replication. The example presented in Section 9 describes the production of an influenza A recombinant virus containing a deletion in the stalk region of the NA gene. This mutant acts as a host range mutant, i.e., a virus that has lost the capability to inflect certain cell types. In another example, the protease of togaviruses, flaviviruses or hepatitis C virus (HCV) could be altered so that appropriate: cleavage of the viral polyprotein is reduced, resulting in a decrease in the number of progeny virions produced during replication.

In another embodiment, viral enzymes involved in viral replication and transcription of viral genes, e.g., viral polymerases, replicases, helicases, etc. may be altered so that the enzyme is less efficient or active. Reduction in such enzyme activity may result in the production of fewer progeny genomes and/or viral transcripts so that fewer infectious particles are produced during replication.

The alterations engineered into any of the viral enzymes include but are not limited to insertions, deletions and substitutions in the amino acid sequence of the active site of the molecule. For example, the binding site of the enzyme could be altered so that its binding affinity for substrate is reduced, and as a result, the enzyme is less specific and/or efficient. For example, a target of choice is the viral polymerase complex since temperature sensitive mutations exist in all polymerase proteins. Thus, changes introduced into the amino acid positions associated with such temperature sensitivity can be engineered into the viral polymerase gene so that an attenuated strain is produced.

6. EXAMPLE: REDUCED TRANSCRIPTION AND REPLICATION OF NA GENE OF INFLUENZA NA/B-NS IS RESPONSIBLE FOR ATTENUATION

In order to understand the molecular characteristics responsible for the attenuation of the transfectant virus, NA/B-NS, the following series of experiments were carried out to analyze the virus at the molecular level. The data presented in the subsections below indicate that attenuation results from the effect of the altered cis elements on the replication of the chimeric NA gene. A low level of the NA gene in the virus preparation results in a higher proportion of defective particles than is found in wild type virus preparation. In addition, the data support a random mechanism for the packaging of vRNAs into influenza virus particles.

6.1. MATERIALS AND METHODS

6.1.1. VIRUSES AND CELLS

The stocks of influenza A/WSN/33 virus and NA/B-NS transfectant virus (Muster et al., 1991, Proc. Natl. Acad. Sci. USA 88: 5177–5181) were prepared from purified plaques by growing them in Madin-Darby bovine kidney (MDBK) cells in reinforced MEM medium (REM) containing 2 $\mu$g/ml trypsin. MDBK cells were used for the plaguing of viruses and the study of virus specific RNA synthesis.

6.1.2. PLASMIDS

In order to generate riboprobes, several plasmids were constructed. pSP64-NS DNA contains the entire NS segment of A/WSN/33 virus inserted into the Sal I site of the pSP64 vector in the orientation by which mRNA sense NS RNA can be made using SP6 RNA polymerase. The fragment derived from pSP64-NS by digestion with Hind III and Eco RI was inserted between the Hind III and the Eco RI site of the IBI30 vector. The resulting plasmid IBI30-NS can produce minus sense NS RNA using T7 RNA polymerase. In order to obtain plasmid ΔT3NAv which produces minus sense NA specific RNA probe, the DNA in the pT3NAv plasmid (Enami et al., 1990, Proc. Natl. Acad. Sci. USA 87: 3802–3805) was shortened by deleting the fragment between the Bam HI and the Eco RI sites. In addition, we created a plasmid designated IBI30-NA by inserting the fragment between the Xba I and Eco RI sites of pT3NAv into the IBI30 vector. This plasmid can generate positive sense NA specific RNA by T7 polymerase transcription.

6.1.3. VIRUS PURIFICATION AND RNA EXTRACTION

Influenza A/WSN/33 virus and NA/B-NS transfectant virus were grown in MDBK cells, and then purified through 30–60% sucrose gradient centrifugation as described previously (Enami et al., 1990, Proc. Natl. Acad. Sci. USA 87: 3802–3805). Virus purified from four 175 cm² flasks of MDBK cells was resuspended in 0.3 ml TMK buffer (10 Mm Tris, pH 7.5, 1.5 mM $MgCl_2$, 10 mM KCl) and disrupted by incubation with 9 $\mu$l 10% SDS and 7.5 $\mu$l proteinase K (10 mg/ml) at 56° C. for 10 minutes, followed by addition of 35 $\mu$l SLN buffer (5% SDS, 1.4 M LiCl, 100 mM NaOAC, pH 7.0). Virion RNAs were extracted with phenol-chloroform and collected by ethanol precipitation. For isolating viral RNAs from infected cells, MDBK cells were infected with either influenza A/WSN/33 virus or NA/B-NS transfectant virus at an m.o.i.=1, and harvested at the indicated time points. Cells were washed twice with ice-cold PBS and lysed with 4 M guanidinium isothiocyanate (Sigma). The total RNA was then purified by equilibrium centrifugation in 5.7 M cesium chloride (Fisher) (Luo et al., 1991, J. Virol. 65: 2861–2867).

6.1.4. DETERMINATION OF THE RATIO OF INFECTIOUS AND PHYSICAL PARTICLES

In order to determine the total number of physical particles of influenza A/WSN/33 virus and NA/B-NS transfectant virus, the virus preparations were mixed with an equal volume of a suspension of carboxylate polystyrene beads (0.1$\mu$in diameter) at a concentration of $4.5 \times 10^9$ particles per milliliter (Polyscience, Inc., Warrington, Pa.), and then stained with phosphotungstic acid. The ratio of virus and polystyrene beads was determined by counting the two different particles under the electron microscope. For measuring the number of infectious particles in the preparations, the virus stocks were serially diluted and plaqued in MDBK cells.

6.1.5. RNA ELECTROPHORESIS

RNAs extracted from influenza A/WSN/33 virus and NA/B-NS transfectant virus were electrophoresed on a 3% polyacrylamide gel containing 7.7 M urea at 150 volts for two hours. The RNA segments were visualized by silver staining as described previously (Enami et al., 1990, Proc. Natl. Acad. Sci. USA 87: 3802–3805).

6.1.6. RIBONUCLEASE PROTECTION ASSAY

Ribonuclease protection assay (RPA) was used for quantitation of virion RNA in viral particles as well as for the measurement of viral mRNAs and cRNAs in infected MDBK cells. The NS segment was chosen as an internal control. For measuring virion RNAs, positive sense NS and NA specific RNA probes were generated by run-off transcription using phase SP6 or T7 RNA polymerase and plasmid PSP64-NS DNA linearized by Nco I and plasmid IBI30-NA digested with Fok I, respectively. To determine the amount of mRNAs and cRNAs, minus sense NS and NA specific RNA probes were transcribed from Dde I digested IBI30-NS DNA and Pvu II cut ΔT3NA DNA, respectively, using phage T7 or T3 RNA polymerase respectively. The RNA probes were labelled with $\alpha^{32}P[UTP]$ (800 Ci/mM, Du Pont, NEN, Boston, Mass.). In general, 50 ng of virion RNA extracted from purified virus was hybridized to $5 \times 10^4$ cpm each of positive sense NS and NA specific probes, or 5 $\mu$g of total RNA isolated from virus-infected cells was hybridized to $5 \times 10^4$ cpm each of minus sense NS and NA specific probes. After 12 hours incubation at 45° C., the hybridization mixture was digested by RNase A/$T_1$, following the manufacturer's instruction (Ambion Inc., Austin, Tex.), and the resulting products were analyzed on a 6% acrylamide denaturing gel (Luo et al., 1990, J. Virol. 64: 4321–4328).

6.1.7. PRIMER EXTENSION

The genomic RNAs (vRNAs) of NA and NS segments of influenza A/WSN/33 virus and of NA/B-NS transfectant virus were quantitated by primer extension (Luo & Taylor, 1990, J. Virol. 64: 4321–4328). The primers for detecting NS and NA specific vRNA are 21 nt long and are complementary to minus sense vRNA. The NS primer, 5'-GGGAACAATTAGGTCAGAAGT-3'(SEQ ID NO: 2) spans the region between nucleotides 695 to 714 of the NS cRNA. The NA primer, 5'-GTGGCAATAACTAATCGGTCA-3'(SEQ ID NO: 3) coves the nucleotides 1151 to 1171 of the NA cRNA. Both NS and NA primers were 5'-end labelled by incubation with $\gamma^{32}$P-ATP (3000 Ci/mM, Du Pont, NEN, Boston, Mass.) and T4 DNA kinase (Biolabs, Beverly, Mass.). 100 ng of RNA extracted from virus or 5 μg of total RNA isolated from infected MDBK cells was reverse transcribed by RNase H minus MLV reverse transcriptase (BRL, Gaithersburg, Md.) in the presence of $3\times10^5$ cpm of each of 5'-end labelled NS and NA primers. After incubation at 37° C. for 2 hours, the reaction was stopped by addition of EDTA to 10 mM, and followed by phenol-chloroform extraction and alkali treatment (Luo & Taylor, 1990, J. Virol. 64: 4321–4328). The products were analyzed on a 6% polyacrylamide gel containing 7 M urea. The amount of product was measured by directly counting the radioactivity of the gel piece corresponding to each band on the film.

6.1.8. NEURAMINIDASE ASSAY AND WESTERN ANALYSIS

For the assay of neuraminidase activity of influenza A/WSN/33 and NA/B-NS transfectant viruses, 2'-(4-methylumbelliferyl)-α-D-N-acetylneuraminic acid (Sigma) was used as substrate. The reaction mixture consisted of 25 μl 2 mM substrate, 25 μl virus and 50 μl 0.2 M phosphate buffer (pH 6.0) containing 2 mM $CaCl_2$. After incubation at 37° C. for 10 minutes, the reaction was stopped by addition of 2 ml 0.5 M glycine-NaOH buffer (pH 10.6), and then the neuraminidase activity was determined by measuring the fluorescence with excitation at 365 nm and emission at 450 nm, using methylumbeliferone as a standard. The protein concentration of the viruses was measured using the Bio-Rad protein assay kit. For the Western analysis of NA and HA proteins of WSN/33 and NA/B-NS viruses, viral proteins were electrophoresed on a 10% Laemmli gel (Laemmli, 1970, Nature 227: 680–685), and subsequently transferred to a nitrocellulose membrane (Schleicher & Schuell, Keene, N.H.). A monoclonal antibody directed against carbohydrates was used to detect the NA and HA glycoproteins of the viruses. The Western blot was developed with a rat antibody against mouse kappa chains which was labelled with $^{125}$Iodine.

6.1.9. ANALYSIS OF PROTEIN SYNTHESIS IN INFECTED CELLS

MDBK cells (35 mm dish) were infected with either WSN/33 virus or NA/B-NS transfectant virus at an moi of approximately 3. This multiplicity was used because the NA/B-NS transfectant virus did not grow to higher titer. At indicated times, the proteins were labelled in cysteine free medium with [$^{35}$S] cysteine (1027 Ci/mmol, Du Pont, NEN Research Products) at 100 μci/ml medium for 30 minutes. The cells were then washed twice with ice-cold PBS buffer and lysed in 150 μl lysis buffer containing 1% NP-40, 150 Mm NaCl, 50 mM Tris-HCl pH 8.0, and 1 mM PMSF. About ¹/₂₀th of the sample was loaded onto a 10% Laemmli gel (Laemmli, 1970, Nature 227: 680–685).

6.2. RESULTS

The results described below indicate that influenza viruses, for which the synthesis of a vRNA segment is down-regulated, produce defective particles during replication. Since the proteins of the NA/B-NS virus are unaltered as compared to wild type virus, attenuation must be the result of inefficient cis-acting signals.

6.2.1. RATIO OF INFECTIOUS TO PHYSICAL PARTICLES

The genome of the transfectant NA/B-NS virus differs from wild type influenza A/WSN/33 virus only in the noncoding region of the NA gene. It is thus likely that the altered biological properties of the transfectant virus are the result of altered cis signals located in the noncoding region of the chimeric NA gene. Specifically, it was noted earlier that the transfectant virus grew to lower titers than wild type virus in MDBK cells, MDCK cells and in mice. In addition, the low multiplicity growth curves in tissue culture were significantly delayed relative to those of wild type virus (Muster et al., 1991, Proc. Natl. Acad. Sci. USA 88: 5177–5181). The transfectant virus was examined for a temperature sensitive phenotype, which could explain the altered growth characteristics. However, the pattern of the growth curve at 30° C., 33° C., 37° C. and 38° C. for NA/B-NS virus was not different from that of wild type virus at the corresponding temperatures. To answer the question of whether defective particles were present in the NA/B-NS virus preparation, the virus was characterized by counting the physical particles under the electron microscope and comparing this number with the plaque-forming units of the preparation. Interestingly, the NA/NS-B transfectant virus showed a similar number of physical particles as wild type virus, but consistently lower PFU titers (Muster et al., 1991, Proc. Natl. Acad. Sci. USA 88: 5177–5181) (Table II).

TABLE II

The ratio of infectious particles to physical particles of influenza A/WSN/33 virus and NA/B-NS transfectant virus.

| Viruses | No. of physical particles (pp) | No. of infectious particles (ip) | Ratio pp/ip |
|---|---|---|---|
| WSN/33 | $1.8 \times 10^9$/ml | $1.2 \times 10^8$/ml | 15 |
| NA/B-NS | $1.2 \times 10^9$/ml | $1.0 \times 10^7$/ml | 120 |

Thus, the NA/B-NS virus grown in MDBK cells shows at least a 5 to 10-fold lower infectious particle to physical particle ratio than is seen with the WSN/33 wild type virus.

6.2.2. CHARACTERIZATION OF THE RNA OF THE ATTENUATED VIRUS

Since the NA/B-NS virus contains many defective particles, the viral RNA was examined for the presence of defective RNAs. Following extraction from purified virus, the genomic RNA was separated on a 3% polyacrylamide gel containing 7.7m urea. As shown in FIG. 2A, the chimeric NA RNA of the NA/B-NS transfectant virus is almost invisible on the gel, whereas the other seven segments are present in approximately equimolar concentrations. When the amount of RNA was increased on the gel, the chimeric NA RNA can be shown to migrate at the same position as the control RNA in FIG. 2A, lane 3. However, electrophoresis and silver staining did not permit the quantitation of the chimeric NA RNA packaged in virions. For this purpose, the ribonuclease protection assay (RPA) and primer extension experiments were performed. Positive sense NS-specific and NA-specific probes were hybridized in the same reaction to purified virion RNA from either WSN/33 virus (FIG. 2A, lane 2) or NA/B-NS transfectant virus (FIG. 2A, lane 3) and then digested by RNase A/T$_1$. The resulting products were analyzed on a 6% polyacrylamide gel containing 7M urea (Luo et al., 1991, J. Virol. 65: 2861–2867), and the amounts of vRNA were calculated by counting the radioactivity of the gel slices corresponding to the bands on the film. As shown in FIG. 2B, the probe protected by the chimeric NA RNA migrates faster than that of the wild type gene because the 5'-noncoding sequences are different in the two NA genes. When compared to the NA segment of WSN/33 virus, the amount of chimeric NA RNA in the transfectant virus is about 6 times lower using the NS gene as an internal control. The primer extension experiment, as shown in FIG. 2C, shows similar reduction of the chimeric NA RNA packaged in virions relative to the NS gene, suggesting a specific lower representation of the chimeric NA gene in the transfectant virus preparation.

6.2.3. CHARACTERIZATION OF THE PROTEIN OF THE ATTENUATED VIRUS

To determine whether or not the NA/B-NS transfectant virus also contained less neuraminidase protein, neuraminidase assays and a Western analysis of the NA protein in virus particles were conducted. For the enzymatic assay of the neuraminidase, the total concentration of viral proteins was first determined by protein assay, and then the same amount of purified virus was used. The NA/B-NS transfectant virus showed only a two-fold lower NA activity than the WSN/33 wild type virus. A similar finding was obtained by Western analysis, which showed 1.9 fold less NA protein, but the same amount of HA protein in virions of the NA/B-NS transfectant virus as compared to those of WSN/33 virus (FIG. 5A).

6.2.4. VIRUS-SPECIFIC RNA SYNTHESIS IN INFECTED CELLS

Based on the vRNA analysis of the NA/B-NS transfectant virus, there is little doubt that less chimeric NA RNA is contained in the viral particles. The lower level of the chimeric NA RNA in the virions could be caused either by a change in the packaging signal leading to less efficient packaging of the NA RNA or by a change in the synthesis of genomic NA RNA which could be the result of inefficient recognition of the influenza B virus specific promoter by the influenza A viral polymerase. To pinpoint the exact mechanism, the synthesis of the chimeric NA gene in infected MDBK cells was examined. Considering that vRNA is mainly synthesized in the late phase of infection (Shapiro et al., 1987, J. Virol. 61: 764–773), RNA was extracted from cells at 7, 8½, and 10 hours post-infection. Five µg of total RNA extracted from virus-infected cells was used for the primer extension analysis. The data in FIG. 4 show that vRNA synthesis of the chimeric NA gene was remarkably decreased relative to that of control virus. When compared to the synthesis of the NA RNA of WSN/33 virus, the chimeric NA gene is reduced by a factor of 9, 8, and 8 at 7, 8½, and 10 hours p.i., respectively. However, no reduction of vRNA synthesis was observed with respect to the NS segment of the NA/B-NS transfectant virus. This result indicates that the reduction of the chimeric NA RNA in transfectant virus is the result of its lower synthesis in cells rather than due to a defect in the packaging of the chimeric NA RNA.

In order to determine the level of mRNA synthesis of the chimeric NA gene, MDBK cells were infected with either WSN/33 virus or NA/B-NS transfected virus, and total RNA was then isolated from virus-infected cells at different times post-infection. Subsequently, the level of virus specific mRNAs was quantitated by RPA. Again the NS segment was used as control (see FIGS. 3A–3C). From the time course, it is apparent that the level of chimeric NA mRNA is markedly reduced relative to that of the wild type virus and that it only increases slightly with time. At 5 hours p.i., the level of chimeric NA mRNA was five-fold less than that of WSN/33 virus (FIG. 3C), whereas the NS-specific mRNA synthesis of the NA/B-NS transfectant virus was similar to that of WSN/33 virus at the indicated times (FIG. 3B). It should be noted that the NS-specific mRNA synthesis appears earlier and is more efficient than NA-specific mRNA synthesis in both WSN/33 and NA/B-NS transfectant virus infected cells (probes of similar activity were used in the experiment). This finding is in good agreement with previous reports (Enami et al., 1985, Virology 142: 68–77), and suggests that the mRNA synthesis of different influenza virus RNA segments is differentially regulated. The conditions of the assay did not permit quantitation of the level of cRNA of the chimeric NA gene because the cRNA synthesis was found to be only 3–5% of that of mRNA synthesis.

6.2.5. REDUCTION OF NA PROTEIN SYNTHESIS IN VIVO

The NA protein was found to be reduced by a factor of two in virions of the NA/B-NS transfectant virus, whereas the synthesis of chimeric NA mRNA was reduced by much more. The question then arose whether the NA protein encoded by the chimeric NA mRNA inside cells parallels the amount of its mRNA, or whether there is a selective incorporation of the neuraminidase into the viral envelope. In order to answer this question, the synthesis of NA protein in infected cells was measured. Viral proteins were labelled with $^{35}$S[cysteine] at 1, 3, 5, and 7 hours post-infection. The cell lysates were then analyzed on a 10% Laemmli gel (Laemmli, 1970, Nature 227: 680–685) and the proteins were quantitated by an AMBIS radioanalytic imaging system (Luo & Taylor, 1990, J. Virol. 64: 4321–4328). As shown in FIG. 5B, synthesis of the NA protein of NA/B-NS transfectant virus was two times lower than that of wild type virus at both 5 and 7 hrs p.i. From this experiment, it can be concluded that the assembly of the NA protein into virions parallels its synthesis in infected cells.

7. EXAMPLE: PANHANDLE BASE PAIRS INVOLVED IN ATTENUATION OF INFLUENZA VIRUS

The experiments described below were designed to identify the nucleotide sequences responsible for attenuation and the effects of gene expression on viral replication.

7.1. MATERIALS AND METHODS

The reverse genetics technique was used to engineer mutations into the panhandle structure of the NA segment of influenza. Viruses and cells were prepared, purified and analyzed for attenuation as described in Section 6.1 and its subsections, supra.

7.2. RESULTS

7.2.1. ATTENUATION SEQUENCE IN THE SECOND STEM STRUCTURE OF THE VIRAL PROMOTER

A series of chimeric mutants constructed and analyzed for attenuation are shown in Table III below. The results indicate that UCCU/AGGA of the NA/DeF/AbC influenza mutant are the critical base pairs involved in attenuation.

7.2.2. REDUCTION IN PROTEIN AND ENZYME ACTIVITY

An additional attenuated mutant, designated NAM-3 has the following structure:

```
        AG.A       A            UUUGAACAAACAUU
   AGU      AAC.. AGGAGUUU
   UCG      UUG   UCCUCAAA
      ...U      CG            CUUAC
```

NAM 3, like NA/B-NS, demonstrates attenuation in that defective particles are produced during each round of replication. However, NAM 3 also demonstrated a ten-fold decrease in neuraminidase expression and enzyme activity (Table IV). This decrease in expression of the enzyme did not affect viral replication.

TABLE IV

NA EXPRESSION AND ACTIVITY IN INFLUENZA VIRUS MUTANT

| | | Enzyme Activity[2] | | |
|---|---|---|---|---|
| Strain | Protein[1] | 10 min | 20 min | 40 min |
| WSN-wt | 1.00 | 3.6 | 5.48 | 5.17 |
| NAM 3 | 0.14 | 0.19 | 0.26 | 0.67 |

[2]Relative intensities of NA bands displayed on SDS-PAGE of infected cells. See Section 6.1.9 for Methods.
[2]Virus was purified over sucrose containing $Ca^{++}$ as described in Section 6.1.3. Enzyme activity was assayed described in Section 6.1.8, and is expressed as percent substrate conversion by 1 ng virus/minute.

8. EXAMPLE: EXPRESSION OF FOREIGN EPITOPES IN THE ANTIGENIC SITES B OR E OF HA OF INFLUENZA RESULTS IN ATTENUATION

The experiments described below indicate that alterations to the B or E region of HA may be engineered to construct attenuated chimeric influenza viruses.

8.1. MATERIALS AND METHODS

The reverse genetics techniques described in Section 6.1.1. supra, were utilized to (a) introduce the malarial epitope (ME 1) of *Plasmodium yoelii*, (NEDSYVPSAEQI) into antigenic site E of the HA of influenza (see FIG. 6A); or (b) to introduce the major antigenic determinant of poliovirus type 1, i.e. the BC loop of the VP1 of poliovirus type 1 (PASTTNKDKL), into antigenic site B of HA of influenza (see FIG. 6B). The $LD_{50}$ of chimeric and wild type influenza was determined in mice by the Karber method (see Muster et al., 1991, Proc. Natl. Acad. Sci. USA 88: 5177–5181).

8.2. RESULTS

The chimeric influenza/malaria virus had a 500- to 1000-fold lower $LD_{50}$ than that of wild type virus when assayed in mice. Likewise the chimeric influenza/polio virus demonstrated a lower $LD_5$.

9. EXAMPLE: DELETIONS AND INSERTIONS OF THE STALK OF THE INFLUENZA VIRUS NEURAMINIDASE: GENERATION OF A HOST RANGE MUTANT

Applying a reverse genetic system, the stalk of the influenza A/WSN/33 virus neuraminidase (NA) gene was altered by making deletions, insertions and mutations in this region of the gene. The data presented in this example show that the length of the NA stalk can be variable. Interestingly, a deletion of 28 amino acids resulted in a host range mutant virus with a markedly reduced growth rate in MDCK cells as compared to that in MDBK cells. Also, an insertion of 41 extra amino acids into the stalk did not significantly interfere with viral growth in either MDCK or MDBK cells, suggesting that the stalk region can tolerate the introduction of long foreign epitopes.

9.1. MATERIALS AND METHODS

9.1.1. CELLS AND VIRUS

Madin-Darby bovine kidney (MDBK) cells were used for RNP transfection. Mardin-Darby canine kidney (MDCK) and MDBK cells were used for preparation of viruses as well as for determination of viral growth characteristics. MDBK cells were grown in reinforced minimal essential medium (REM) (Whittaker, Walkersville, Md.) supplemented with 10% FCS (GIBCO, Gaithersburg, Md.), and MDCK cells were grown in minimal essential medium (MEM) (Whittaker) containing 10% FCS (GIBCO). MDBK and MDCK cells were maintained in REM and MEM containing 0.42% bovine albumin (BA), respectively. Influenza WSN-HK (H1N2) virus, a reassortant virus, was used for the RNP transfection experiment (Enami, et al., 1990, Proc. Natl. Acad. Sci. USA 87:3802–3805). This virus has the NA gene of influence A/Hong Kong/8/68 virus and other seven RNA segments from A/WSN/33 virus, and it does not grow in MDBK cells in the absence of trypsin. WSN-HK virus was propagated in 11 day old embryonated hens' eggs and titrated in MDCK cells.

9.1.2. CONSTRUCTION OF NA MUTANTS

Clone pT3NAv which contains the cDNA of the influenza A/WSN/33 virus NA gene was described previously (Enami et al. 1990, Proc. Natl. Acad. Sci. USA 87:3802–3805). No unique restriction enzyme site was found in the region encoding the stalk of the NA protein. In order to facilitate the manipulation of the stalk of the NA, plasmid pT3NAv had to be modified. One of the choices was destroy the Sty I/Dsa I site at nucleotide 875 so that the Sty I site at nucleotide 169 and the Dsa I site at nucleotide 253 became unique. For achieving this, the pT3NAv DNA was cut by Nco I at nucleotide 875 and trimmed with mungbean nuclease using standard methods (Sambrook et al., 1989, Molecular Cloning: A Laboratory Manual, 2nd ed., Cold Spring Harbor Laboratory Press, Cold Spring Harbor, N.Y.). The DNA was then digested by Pst I at nucleotide 926. The fragment between nucleotides 875 and 926 was replaced by a polymerase chain reaction (PCR) fragment in which nucleotide 877 was changed by a silent mutation. The PCR fragment was made (Erlich, 1989, PCR Technology: Principles and Applications for DNA Amplification, Stockton Press) using pT3NAv as template and oligonucleotides NA01 and NA02 as primers (Table V). After digestion with Pst I, the PCR fragment was ligated into the pT3NAv DNA which was digested by both Nco I and Pst I. The modified pT3NAv was called pT3NAmod. Using the pT3NAmod clone, a series of NA mutants with deletions, insertions and mutations in the stalk region of the NA protein were generated. The oligonucleotides used for making these constructs are shown in Table V:

TABLE V

CONSTRUCTION OF NA MUTANTS

| Mutants | | Oligonucleotides | Method of Construction* |
|---|---|---|---|
| T3NAmod | NA01 (SEQ ID NO:5) | 5'-CCTGGGTGTCCTTC-3' | PCR |
| | NA02 (SEQ ID NO:6) | 5'-CCCCACTGCAGATG-3' | |
| Del 16 | NA03 (SEQ ID NO:7) | 5'-CAAGGCAGCACCGGCAA CTCGAGTCTTTGTCCATC-3' | Annealing |
| | NA04 (SEQ ID NO:8) | 5'-CACGGATGGGACAAAGA CTCGAGTTGCCGGTGCTGC-3' | |
| Del 18m | NA05 (SEQ ID NO:9) | 5'-GCGCGCTCGAGAGGCTGCC TTGG-3' | PCR |
| | M 13 (SEQ ID NO:10) | 5'-GTAAAACGACGGCCAGT-3' | |
| Del 23N | NA06 (SEQ ID NO:11) | 5'-GCGCGCTCGAGTTGCCGGTA GTATGGTTTTG-3' | PCR |
| | M 13 | See Above | |
| Del 23C | NA07 (SEQ ID NO:12) | 5'-GCGCGCCACGGCAAAGAGATGA ATTGTTGCATATTCC-3 | PCR |
| | M13 | See Above | |
| Del 28N | NA08 (SEQ ID NO:13) | 5'-GCGCGCTCGAGTTGCCGGTTC CGGTTTGAAT-3 | PCR |
| | M13 | See Above | |
| N72Q/ C76S | NA09 (SEQ ID NO:14) | 5'-GCGCGCCACGGATGGGCGAAAGA GATGATTGGCCGGTTAATATC-3' | PCR |
| | M13 | See Above | |
| Ins 12 | NA10 (SEQ ID NO:15) | 5'-CTTGGATGGGACAAAGACTCGAG TTGCCGGTGCTGC-3' | Annealing |
| | NA03 | See Above | |
| Ins 41 | NA11 (SEQ ID NO:16) | 5'-GCGCGCCGTGGGACCGGAA ATC-3' | PCR |
| | NA12 (SEQ ID NO:17) | 5'-AGCCCACCCACGG-3' | |

*For all PCR reactions, pT3NAV was used as template.
The underlined nucleotides indicate the position of a newly created Ava 1 site.

Del 16 was created by replacing the fragment between the Sty I and Dsa I sites in pT3NAmod with the annealed oligonucleotides NA03 and NA04. Through silent mutations, a unique Ava I site was created in plasmid Del 16 (underlined nucleotides in Table V). Mutant Del 18m, Del 23N and Del 28N was made by PCR using pT3NAv as template and M13/Puc forward sequencing primer (5'-GTAAAACGACGGCCAGT-3'SEQ ID NO: 10) and NA05, NA06 and NA08 as primer, respectively. The PCR products were digested by EcoR I and Ava I and inserted into plasmid Del 16 DNA which was digested by the same enzymes. Mutant Del 23C and N72Q/C76S were also made by PCR in the same way except for using NA07 and NA09 as primer, respectively. The PCR products were digested with Dsa I and Eco RI, and inserted into pT3NAmod digested with the same enzymes. Ins. 12 and Ins 24 were obtained by inserting the annealed oligonucleotides NA03 and NA10 into the Sty I site of pT3NAmod. Ins 24 contains a duplicate of the insertion present in Ins 12. Ins 41 was made by PCR using pT3NAv as template and oligonucleotides NA11 and NA12 as primers. The PCR fragment was digested by Dsa I and inserted into the Dsa I site of pT3NAmod. In order to make Del 28 C, plasmid pT3NAmod was cut by Dsa I, and filled-in with reverse transcriptase (BRL, Bethesda, Md.). The DNA was then digested by Sty I, trimmed with mung-bean nuclease and blunt-end ligated.

9.1.3. RNP TRANSFECTION

The RNP transfection experiments were carried out by using the standard protocol as reported before (Enami and Palese, 1991, J. Virol. 65:2711–2713). Briefly, the plasmid DNAs were digested by restriction enzyme Ksp6321 or Ear I. 1 µg linearized DNA was incubated in 10 µl viral nucleoprotein and polymerase proteins (approximately 1 µg) isolated from influence A/PR/8/34 virus and 100 U T3 RNA polymerase (Stratagene, La Jolla, Calif.) in a 50 µl volume under transcription conditions. The in vitro reconstituted RNP complex was then transfected into MDBK cells which were infected with WSN-HK reassortant virus at an mode of infectivity (m.o.i.)=1. At 20 hours post infection, the supernatant was collected and used for plaque assay in MDBK cells in order to select the transfectant virus.

9.1.4. VIRUS PREPARATION AND RNA EXTRACTION

Transfectant viruses were isolated and amplified from individual plaques in MDBK cells. Then viruses were propagated in 175 $cm^2$ large flasks of MDCK cells, and purified through 30–60% sucrose gradients. Virion RNA was extracted from purified viruses as described previously (Luo et al., 1992, J. Virol. 66:4679–4685).

9.1.5. ELECTROPHORESIS AND SILVER STAINING OF vRNA SEGMENTS

The vRNA extracted from viruses was analyzed on a 2.8% acrylamide gel containing 7.7 M urea. The vRNA segments were then visualized by silver staining as reported before (Enami et al., 1990, Proc. Natl. Acad. Sci. USA 87:3802–3805).

9.1.6. REVERSE TRANSCRIPTION AND PCR

The NA-specific RNA of the viruses containing wild type NA or Del 18m, Del 23N and Del 28N mutant NAs were transcribed by reverse transcriptase (BRL, Bethesda, Md.) using oligonucleotide 5'-GTCAATCTGTATGGTAGTCGG-3'(SEQ ID NO: 18) as primer, which covers nucleotide 52 to nucleotide 72. The reverse transcripts were amplified by PCR using the above oligonucleotide and oligonucleotide NA12 (Table V) as primers (Luo et al., 1991, J. Virol. 65:2861–2867). Primer NA12 was labelled with gamma $^{32}$[P]ATP. The PCR products were denatured by alkali and analyzed on a 6% polyacrylamide gel containing 7 M urea.

9.1.7. GROWTH CURVE

MDBK and MDCK cells were infected with wild type virus and each of the transfectant viruses at an m.o.i.=0.001, and maintained in REM and MEM media containing 0.5 µg/ml trypsin. Supernatants were collected at 12, 24, 36 and 48 hour postinfection. The number of plaque forming units (PFU) of each supernatant was determined by plaque assay in MDBK cells.

9.2. RESULTS

The influenza virus neuraminidase (NA) protein functions during the infectious cycle as an enzyme to remove terminal sialic acids. Its action may prevent self-aggregation of virus particles, and promote virus release during budding from host cells (Palese et al., 1974, Virol. 61:397–410). NA is an integral membrane glycoprotein anchored in the viral membrane as a homo-tetramer. Each tetrameric NA appears as a mushroom-shaped spike (FIG. 7) on the surface or the virion when viewed in the electron microscope (Laver and Valentine, 1969, Virol. 38:105–119; Wrigley et al., 1973, Virol. 51:525–529). Structurally, the monomer of the NA consists of four different domains (FIG. 7): a cytoplasmic and a transmembrane domain, the thin stalk, and the globular head (Blok and Air, 1982, Biochem. 21:4001–4007; Colman, 1989, in "The Influenza Viruses", R. M. Krug, ed., pp. 175–218, Plenum Press, New York). Although much is known about the structure and role of the head region, the structure-function relationship of the stalk region is less well understood. Presented below is a study of the stalk region of the NA in which the length and structure of the stalk is varied by deletions, insertions and mutations.

9.2.1. RESCUE OF DELETION MUTANTS OF NA INTO INFECTIOUS VIRUS

Based on sequence comparisons of different influenza A virus NA genes, it has been suggested that the stalk region of the NA varies between 25 and 57 amino acids (Blok and Air, 1982, Biochem. 21:4001–4007; Blok and Air, 1982, Virol. 118:229–234; Els et al., 1985, Virol. 142:241–247; Colman, 1989, in "The Influenza Viruses", R. M. Krug, ed., pp. 175–218, Plenum Press, New York ). The stalk region of the influenza A/WSN/33 virus NA, which was used in this study, is approximately 41 amino acids long (Blok and Air, 1982, Biochem. 21:4001–4007; Blok and Air, 1982, Virol. 118:229–234; Hiti and Hagar, 1982, J. Virol. 41:730–734; Colman, 1989, in "The Influenza Viruses", R. M. Krug, ed., pp. 175–218, Plenum Press, New York). It was first asked whether NA mutants with large deletions could be rescued into infectious virus particles. The first mutant gene, Del 16, (SEQ ID NO: 27) that was constructed lacked 48 nucleotides (amino acid position 53–69) (FIG. 8), and following RNP transfection infectious virus was isolated. Purified RNA was separated on a 2.8% acrylamide gel containing 7.7 M urea and the NA segment with the 48 nucleotide deletion (Del 16) was shown to migrate faster than the NA RNA of the wild type virus (FIG. 9: compare lane 1 and lane 2). This suggested that influenza A/WSN/33 virus can tolerate a neuraminidase with a stalk of only about 25 amino acids. A gene encoding an NA with a 28 amino acid deletion (Del 28C, (SEQ ID NO: 28) FIG. 8) was then constructed. After RNP transfection, however, no infectious virus was rescued. This result could be either due to the truncation of the stalk region or due to the deletion of a potential glycosylation site at position 74 and/or of a cysteine at position 76. Since the potential glycosylation site and the cysteine residue are highly conserved among different NAs (Blok and Air, 1982, Biochem. 21:4001–4007), the possibility was first explored that important structural elements were destroyed by this deletion. For this purpose, three other NA mutants were constructed: N72Q/C76S, Del 23C, and Del 18m (SEQ ID NO: 29) (FIG. 8). In the N72Q/C76S mutant, the asparagine (N) at position 72 and the cysteine (C) at position 76 were mutated into glutamine (Q) and serine (S), respectively. Although this gene has the same length of the stalk as the wild type gene, no infectious virus could be rescued. To dissect the contribution of the glycosylation site and of the cysteine residue, mutant Del 18m was constructed by changing the asparagine at position 72 to leucine and deleting amino acids 53 to 71. Interestingly, infectious progeny virus was obtained following RNP transfection of the Del 18m NA RNA. This finding suggests that the cysteine at position 76, rather than the potential glycosylation site at position 72 is essential for the formation of infectious virus. However, it was not clear whether or not deletions beyond the cysteine can be tolerated. Thus mutant Del 23C (SEQ ID NO: 30)

was designed in which the potential glycosylation site and the cysteine were reintroduced into the NA but two amino acids C-terminal to the cysteine were deleted. No virus containing the Del 23C mutant gene was obtained. It thus appears that the sequence following the stalk region does not tolerate deletions, suggesting that this region is part of the NA "head". However, the possibility could not be ruled out that the Del 23C mutant virus was non-infectious due to the further shortening of the NA stalk by 5 amino acids. Two more constructs were therefore created: Del 23N (SEQ ID NO: 31) and Del 28N (SEQ ID NO: 32). The Del 23N mutant has a 23 amino acid deletion between amino acid 47 and 69, and the Del 28N mutant has a 28 amino acid deletion starting at amino acid 42 and extending to amino acid 69. Both Del 23N and Del 28N resulted in infectious influenza viruses. This suggests that an NA stalk of approximately 12 amino acids suffices to generate infectious virus. The deletion analysis was not extended further because the virus containing the Del 28N mutant NA does not grow as well as wild type virus (see below), and has a deletion that leaves only a few amino acids near the viral membrane at the N-terminal and the cysteine at the C-terminal side. In order to verify that the NA RNAs of the mutant viruses had truncated stalk regions, the NA specific RNAs were reverse transcribed and analyzed by PCR using a labelled primer. The sizes of the PCR products of wild type, Del 18m, Del 23N and Del 28N were as expected (FIG. 10, lanes 2–5).

9.2.2. RESCUE OF INSERTION MUTANTS OF NA INTO INFECTIOUS VIRUS

The deletion analysis revealed that the length of the NA stalk is flexible. Virus is still viable even when it contains an NA whose stalk region is almost completely deleted. The question, however, remained as to whether or not the stalk of the NA molecule can tolerate the insertion of extra amino acids. To answer this 12 and 24 amino acids were inserted into the stalk region of the NA between amino acids 50 and 51, as shown in FIG. 8 (Ins. 12 (SEQ ID NO: 33) and Ins. 24 (SEQ ID NO: 34), respectively). After RNP transfection, both Ins 12 and Ins 24 mutant NA RNAs were rescued into infectious transfectant viruses. The fact that these two NA mutants were viable, led the insertion of additional amino acids. To that end, mutant Ins 41 NA was generated by inserting 41 amino acids between position 39 and 40. The Ins 41 (SEQ ID NO: 35) mutant contains a duplication in the NA stalk. A gain, infectious virus was rescued, indicating that the NA stalk tolerates a 41 amino acid insertion. The purified RNAs of Ins 12, Ins 24 and Ins 41 mutant viruses were analyzed on a polyacrylamide gel and the rescued NA RNAs were found to migrate in the expected positions (FIG. 9, lanes 3, 4, and 5).

9.2.3. GROWTH CHARACTERISTICS OF THE NA TRANSFECTANT VIRUSES

In order to determine whether deletions and insertions in the stalk region of the NA molecule have effects on virus growth, the transfectant viruses were characterized in MDBK and MDCK cells. The results are shown in FIGS. 11A–11B. Since all mutant viruses were rescued by isolating progeny viruses in MDBK cells to allow selection against the helper virus, it is not surprising that all mutants grow in this cell type (FIG. 11A). It appears that mutant Del 28N and mutant Ins 24 grow slightly slower and to lower titers than do either the remaining mutants or the wild type virus. It should also be noted that the MDBK cell line currently in use yields lower overall titers than other MDBK cell lines. The yields in MDCK cells (FIG. 11B) are higher by approximately one log, except those of mutant Del 18m and mutant Del 28N, which grow to $10^2$ and $10^4$ time lower titers, respectively, than does wild type virus. Mutant Del 28N is thus a host range mutant which grows about 1,000 times less efficiently in MDCK cells as compared to MDBK cells.

The present invention is not to be limited in scope by the specific embodiments described which are intended as single illustrations of individual aspects of the invention, and any constructs or viruses which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

What is claimed is:

1. An attenuated genetically engineered double-stranded segmented RNA virus containing at least one modification in the conserved sequences of the 5' or 3' termini of a viral gene segment that down-regulates transcription of at least one viral gene encoded by the gene modified segment, and results in the production of fewer progeny virions than would be generated by a corresponding wild type virus.

2. The attenuated virus of claim 1 which belongs to the reovirus family.

3. The attenuated virus of claim 2 in which a viral non-structural gene is modified.

4. The attenuated virus of claim 1 in which the modified termini down-regulates transcription of the viral envelope gene.

5. The attenuated virus of claim 1 in which the modified termini down-regulates transcription of the viral protease gene.

6. The attenuated virus of claim 1 in which the modified termini down-regulates transcription of the viral polymerase gene.

* * * * *